(12) United States Patent
Porter et al.

(10) Patent No.: US 11,752,015 B2
(45) Date of Patent: Sep. 12, 2023

(54) FAILSAFE DEVICE FOR PROSTHETIC LIMB

(71) Applicant: Biomet Manufacturing, LLC, Warsaw, IN (US)

(72) Inventors: Joshua R. Porter, Winona Lake, IN (US); Mark Roberts, Plymouth, IN (US); Jason S. Toler, Pierceton, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 410 days.

(21) Appl. No.: 16/991,601

(22) Filed: Aug. 12, 2020

(65) Prior Publication Data

US 2020/0368042 A1 Nov. 26, 2020

Related U.S. Application Data

(63) Continuation of application No. 15/856,566, filed on Dec. 28, 2017, now Pat. No. 10,772,745.

(Continued)

(51) Int. Cl.
*A61F 2/78* (2006.01)
*A61F 2/68* (2006.01)

(52) U.S. Cl.
CPC ........ *A61F 2/78* (2013.01); *A61F 2002/6845* (2013.01); *A61F 2002/7887* (2013.01)

(58) Field of Classification Search
CPC ................ A61F 2/78; A61F 2002/7887; A61F 2002/6845
See application file for complete search history.

(56) References Cited

U.S. PATENT DOCUMENTS 125,539 A * 4/1872 Callen ..................... E05B 85/22
  292/173
2,696,649 A  12/1954 Clapper
(Continued)

FOREIGN PATENT DOCUMENTS

EP    2194906 B1   3/2015
NL    2010991 C    12/2014
(Continued)

OTHER PUBLICATIONS

"U.S. Appl. No. 15/856,566, Advisory Action dated Apr. 17, 2020", 4 pgs.
(Continued)

*Primary Examiner* — Christie Bahena
(74) *Attorney, Agent, or Firm* — Schwegman Lundberg & Woessner, P.A.

(57) ABSTRACT

A failsafe for a transdermal apparatus for a prosthetic appendage can include a first plate, a second plate, and a breakaway connector. The first plate can have a central axis, a proximal portion, and a distal end. The distal end can be opposite the proximal portion, and the distal end can be securable with a prosthetic external to skin and can be configured to simulate an appendage of a patient. The second plate can be aligned with the central axis and can include a proximal end and a distal portion. The proximal end can be securable to a transdermal implant, and can extend proximally from the second plate. The distal portion can be opposite the proximal end, and the distal portion can be configured to interface with the proximal portion of the first plate. The breakaway connector can be couplable within the second plate and the first plate.

20 Claims, 14 Drawing Sheets

Related U.S. Application Data

(60) Provisional application No. 62/462,593, filed on Feb. 23, 2017, provisional application No. 62/442,760, filed on Jan. 5, 2017.

(56) References Cited

U.S. PATENT DOCUMENTS

| | | | |
|---|---|---|---|
| 4,573,717 | A | 3/1986 | Peacock |
| 4,705,305 | A | 11/1987 | Ghaly |
| 5,479,836 | A | 1/1996 | Chang |
| 7,473,234 | B1 * | 1/2009 | Weltner .................. A61F 5/013 602/5 |
| 8,268,011 | B2 | 9/2012 | Newcombe et al. |
| 10,369,026 | B2 | 8/2019 | Toler |
| 10,772,745 | B2 | 9/2020 | Porter et al. |
| 2002/0149123 | A1 | 10/2002 | Edel et al. |
| 2005/0049720 | A1 | 3/2005 | Benson |
| 2008/0288087 | A1 | 11/2008 | Bachus et al. |
| 2011/0190907 | A1 | 8/2011 | Porter et al. |
| 2015/0164659 | A1 | 6/2015 | Konishi |
| 2015/0257904 | A1 | 9/2015 | Brnemark et al. |
| 2018/0014951 | A1 | 1/2018 | Toler |
| 2018/0185174 | A1 | 7/2018 | Porter et al. |
| 2021/0015578 | A1 | 1/2021 | Marchese |
| 2022/0395343 | A1 | 12/2022 | Lemieux et al. |

FOREIGN PATENT DOCUMENTS

| | | |
|---|---|---|
| WO | WO-2007018904 A2 | 2/2007 |
| WO | WO-2013141777 A1 | 9/2013 |
| WO | WO-2018128903 A1 | 7/2018 |
| WO | WO-2019177569 A1 | 9/2019 |
| WO | WO-2021005177 A1 | 1/2021 |

OTHER PUBLICATIONS

"U.S. Appl. No. 15/856,566, Final Office Action dated Jan. 30, 2020", 13 pgs.
"U.S. Appl. No. 15/856,566, Non Final Office Action dated Sep. 20, 2019", 9 pgs.
"U.S. Appl. No. 15/856,566, Notice of Allowance dated May 12, 2020", 5 pgs.
"U.S. Appl. No. 15/856,566, Response filed Mar. 30, 2020 to Final Office Action dated Jan. 30, 2020", 12 pgs.
"U.S. Appl. No. 15/856,566, Response filed Apr. 30, 2020 to Advisory Action dated Apr. 17, 2020", 12 pgs.
"U.S. Appl. No. 15/856,566, Response filed Dec. 18, 2019 to Non Final Office Action dated Sep. 20, 2019", 11 pgs.
"European Application Serial No. 17832703.7, Communication Pursuant to Article 94(3) EPC dated Jun. 24, 2020", 5 pgs.
"European Application Serial No. 17832703.7, Response to Communication pursuant to Rules 161(1) and 162 EPC filed Feb. 21, 2020", 12 pgs.
"International Application Serial No. PCT/US2017/068696, International Preliminary Report on Patentability dated Jul. 18, 2019", 7 pgs.
"International Application Serial No. PCT/US2017/068696, International Search Report dated May 4, 2018", 4 pgs.
"International Application Serial No. PCT/US2017/068696, Written Opinion dated May 4, 2018", 5 pgs.
"OPRA Implant System Product Catalouge", Intergrum AB, (accessed Apr. 17, 2018), 8 pgs.
"U.S. Appl. No. 15/647,605, Corrected Notice of Allowability dated Apr. 19, 2019", 10 pgs.
"U.S. Appl. No. 15/647,605, Notice of Allowance dated Feb. 20, 2019", 13 pgs.
"U.S. Appl. No. 15/647,605, Response filed Jan. 31, 2019 to Restriction Requirement dated Dec. 18, 2018", 7 pgs.
"U.S. Appl. No. 15/647,605, Restriction Requirement dated Dec. 18, 2018", 7 pgs.
"U.S. Appl. No. 15/856,566, Corrected Notice of Allowability dated Aug. 20, 2020", 2 pgs.
"European Application Serial No. 17832703.7, Communication Pursuant to Article 94(3) EPC dated Mar. 24, 2021", 5 pgs.
"European Application Serial No. 17832703.7, Response filed Nov. 4, 2020 to Communication Pursuant to Article 94(3) EPC dated Jun. 24, 2020", 17 pgs.
"European Application Serial No. 17832703.7, Response filed Sep. 16, 2021 to Communication Pursuant to Article 94(3) EPC dated Mar. 24, 2021", 15 pgs.
"European Application Serial No. 22179062.9, Extended European Search Report dated Nov. 10, 2022", 9 pgs.

\* cited by examiner

FAILSAFE DEVICE FOR PROSTHETIC LIMB

CLAIM OF PRIORITY

This application is a continuation of U.S. patent application Ser. No. 15/856,566, filed on Dec. 28, 2017, which claims the benefit of U.S. Provisional Patent Application Ser. No. 62/442,760, filed on Jan. 5, 2017, and U.S. Provisional Patent Application Ser. No. 62/462,593, filed on Feb. 23, 2017, the benefit of priority of each are claimed hereby, and which are incorporated by reference herein in their entireties.

FIELD

The present subject matter relates to orthopedic prostheses and, more particularly, to prostheses, systems and methods used with prosthetic limbs.

BACKGROUND

Orthopedic procedures and prostheses are commonly utilized to repair and/or replace damaged bone and tissue in the human body. For example, a below the knee or above the knee amputation may also include installation of an implant anchored to a tibia or a femur of a patient. The implant may include a transdermal component that can extend through the skin of the patient for connecting to a prosthetic limb or appendage. The prosthetic limb (or prosthetic leg) can improve a patient's quality of life, allowing, in some cases, the patient to run, walk, and jump.

OVERVIEW

This disclosure pertains generally to prostheses, systems, and methods for protecting femoral implants securable to limb prostheses. The present inventors have recognized, among other things, that a patient may use a prosthetic limb in situations where accidents or misuse can arise. In such cases, forces, torques, and moments can be transferred between a prosthetic and a limb or appendage which can cause damage of an implant or appendage. Regardless of the cause of the force, it is generally desirable to avoid transferring damaging forces and moments to appendages and implanted devices. In some cases, fail safes can be used to prevent the transfer of these forces between prosthetics and appendages. In prior cases, failsafes have been used to limit transmission of moments about a single plane, such as a posterior/anterior plane. However with this solution, appendages and their implants are susceptible to the transmission of forces in a medial/lateral plane, or any force transferred from a plane between the medial/lateral plane and the posterior/anterior plane. Thus, the present inventors propose a failsafe device and system that includes a breakaway connector configured to prevent the transmission of forces in a medial/lateral plane, an anterior/posterior plane, or any force transferred from a plane between the medial/lateral plane and the posterior/anterior plane. Further, the inventors propose a failsafe device that includes torsion protection that operates and is adjustable independent from the moment protection.

To further illustrate the apparatuses and systems disclosed herein, the following non-limiting examples are provided:

Example 1 is a failsafe for a transdermal apparatus for a prosthetic appendage, the failsafe comprising: a first plate having a central axis, the first plate comprising: a proximal portion; and a distal end securable with a prosthesis configured to be disposed external to skin, the prosthesis configured to simulate an appendage of a patient; a second plate alignable with the central axis, the second plate comprising: a proximal end securable to a transdermal implant, the proximal end extending proximally from the second plate; and a distal portion configured to interface with the proximal portion of the first plate; and a breakaway connector coupleable within the second plate and the first plate and configured to allow the second plate to break away from the first plate when a moment applied to both the first and the second plate is larger than a threshold moment.

In Example 2, the subject matter of Example 1 optionally includes wherein the breakaway connector is configured to engage the distal portion of the second plate with the proximal portion of the first plate.

In Example 3, the subject matter of any one or more of Examples 1-2 optionally include wherein the breakaway connector is secured to the second plate and is configured to break away from the first plate.

In Example 4, the subject matter of Example 3 optionally includes a fastener engageable with the breakaway connector to secure the breakaway connector to the first plate and the second plate.

In Example 5, the subject matter of any one or more of Examples 1-4 optionally include wherein the breakaway connector is secured to the first plate and is configured to break away from the second plate.

In Example 6, the subject matter of Example 5 optionally includes a plurality of recesses in the proximal portion of the first plate; and a plurality of retaining members extending from the second plate and configured to engage the recesses to transfer torque between the first plate and second plate when a torque is below a threshold torque and configured to disengage from the recesses and allow rotation of the first plate relative to the second plate when an applied torque is above the threshold torque.

In Example 7, the subject matter of any one or more of Examples 1-6 optionally include wherein the moment can be applied in any plane of the device, and wherein the breakaway connector is configured to cause the second plate to separate from the first plate due to the moment when the moment in any plane is greater than the threshold moment.

In Example 8, the subject matter of any one or more of Examples 1-7 optionally include wherein the breakaway connector further comprises: a base; and a plurality of arms projecting axially from the base and extending between the second plate and the first plate.

In Example 9, the subject matter of Example 8 optionally includes wherein the plurality of arms each comprise a prong disposed at a termination of each arm, each prong extending radially outward from each arm to create a radial extension.

In Example 10, the subject matter of any one or more of Examples 8-9 optionally include wherein each radial extension of each prong is configured to engage a radial surface of a counterbore of one of the first plate and the second plate to engage the first plate and the second plate.

In Example 11, the subject matter of any one or more of Examples 8-10 optionally include wherein the plurality of arms are configured to reversibly deflect radially inward, allowing the second plate to break away from the first plate when the arms deflect radially inward.

In Example 12, the subject matter of any one or more of Examples 1-11 optionally include the second plate further comprising: an opening at the proximal end of the second plate configured to receive the transdermal implant therein.

In Example 13, the subject matter of Example 12 optionally includes an arm pivotably coupled to the top plate proximate the proximal end, the arm pivotable between an open position and a closed position.

In Example 14, the subject matter of Example 13 optionally includes a cam and lever coupled to the proximal end, the lever movable to actuate the cam and tighten the arm to secure the transdermal implant to the second plate.

In Example 15, the subject matter of Example 14 optionally includes the arm further comprising: a flange extending radially and including eye configured to receive the cam therethrough.

In Example 16, the subject matter of Example 15 optionally includes a biasing element engageable with the flange and the lever to bias the arm toward the open position.

In Example 17, the subject matter of Example 16 optionally includes wherein the biasing element is a spring disposed around the cam.

In Example 18, the subject matter of Example 17 optionally includes the top plate further comprising: a slot configured to receive at least a portion of the arm therein to secure the transdermal implant to the top plate.

In Example 19, the subject matter of Example 18 optionally includes a nut engageable with the cam to adjust a distance that the arm extends into the slot in the closed position to adjust a clamping force applied by the arm to the transdermal implant.

In Example 20, the subject matter of any one or more of Examples 13-19 optionally include a pin coupling the arm to the proximal end, the arm pivotable about the pin.

Example 21 is a failsafe for a transdermal apparatus for a prosthetic appendage, the failsafe comprising: a first plate having a central axis, the first plate comprising: a proximal portion; and a distal end opposite the proximal portion, the distal end securable with a prosthetic external to skin and configured to simulate an appendage of a patient; a second plate aligned with the central axis, the second plate comprising: a proximal end securable to a transdermal implant, the proximal end extending proximally from the second plate; and a distal portion opposite the proximal end, the distal portion configured to interface with the proximal portion of the first plate; and a breakaway connector coupleable within the second plate and the first plate and configured to engage the distal portion of the second plate with the proximal portion of the first plate, and configured to allow the second plate to break away from the first plate when a moment applied to first and second plate is larger than a threshold moment.

In Example 22, the subject matter of Example 21 optionally includes wherein the breakaway connector is secured to the second plate and is configured to break away from the first plate.

In Example 23, the subject matter of Example 22 optionally includes a fastener passing through the breakaway connector securing the breakaway connector to one of the first and second plate.

In Example 24, the subject matter of any one or more of Examples 21-23 optionally include wherein the breakaway connector is secured to the first plate and is configured to break away from the second plate.

In Example 25, the subject matter of any one or more of Examples 21-24 optionally include an opening at the proximal end of the second plate configured to receive the transdermal implant; a collar disposed within the opening and configured to surround a distal portion of the transdermal implant, and a cam and lever coupled to the proximal end, the lever movable to actuate the cam and tighten the collar to secure the transdermal implant to the second plate.

In Example 26, the subject matter of Example 25 optionally includes a plurality of recesses in the proximal portion of the first plate; and a plurality of retaining members extending from the second plate and configured to engage the recesses to transfer torque between the first plate and second plate when a torque is below a threshold torque and configured to disengage from the recesses and allow rotation of the first plate relative to the second plate when the torque is above the threshold torque.

In Example 27, the subject matter of any one or more of Examples 21-26 optionally include wherein the breakaway connector is configured to cause the second plate to separate from the first plate due to a moment applied in any plane that is greater than the threshold moment.

In Example 28, the subject matter of Example 27 optionally includes wherein the breakaway connector further comprises: a base; and a plurality of arms projecting axially from the base and extending between the second plate and the first plate.

In Example 29, the subject matter of Example 28 optionally includes wherein the plurality of arms each comprise a prong disposed at a termination of each arm, each prong extending radially outward from each arm.

In Example 30, the subject matter of any one or more of Examples 28-29 optionally include wherein the plurality of arms are configured to reversibly deflect radially inward, and allow the second plate to break away from the first plate when the arms deflect radially inward.

Example 31 is a failsafe for a transdermal apparatus for a prosthetic appendage, the failsafe comprising: a first plate comprising: a proximal portion; and a distal end opposite the proximal portion, the distal end securable with a prosthetic external to skin and configured to simulate an appendage of a patient; a second plate comprising: a proximal end securable to a transdermal implant, the proximal end extending proximally from the second plate; and a distal portion opposite the proximal end, the distal portion configured to interface with the proximal portion of the first plate; and a breakaway connector secured to the first plate and releasably coupled to the second plate to engage the distal portion of the second plate with the proximal portion of the first plate, and configured to allow the second plate to break away from the first plate when a moment applied to first and second plate is larger than a threshold moment.

In Example 32, the subject matter of Example 31 optionally includes a plug threadable into a bore of the transdermal implant to seal the transdermal implant from an external environment.

In Example 33, the subject matter of any one or more of Examples 31-32 optionally include a first retainer bore extending through the first plate; and a retainer securable within the retainer bore and engageable with the breakaway connector to secure the breakaway connector within the first plate.

In Example 34, the subject matter of Example 33 optionally includes the breakaway connector further comprising: a circumferential groove configured to receive the retainer.

In Example 35, the subject matter of any one or more of Examples 33-34 optionally include wherein the retainer is configured to draw the breakaway connector away from the second plate to engage a radial surface of a coaxial counterbore of the first plate and secure the second plate to the first plate.

In Example 36, the subject matter of any one or more of Examples 33-35 optionally include wherein the first plate further comprises: a plurality of retainer bores extending through the first plate and including the first retainer bore, wherein the retainer is securable within each of the plurality of retainer bores.

In Example 37, the subject matter of Example 36 optionally includes a plurality of retainer fasteners, each securable within each of the plurality of retainer bores.

In Example 38, the subject matter of any one or more of Examples 35-37 optionally include a plurality of recesses in the distal portion of the second plate; and a plurality of retaining members extending from the first plate and configured to engage the recesses to transfer torque between the first plate and second plate when a torque is below a threshold torque and configured to disengage from the recesses and allow rotation of the first plate relative to the second plate when the torque is above the threshold torque.

In Example 39, the subject matter of Example 38 optionally includes a plurality of spring bores extending through the first plate from the distal end to the proximal portion; and a plurality of springs disposable within the plurality of spring bores, the plurality of springs engageable with the plurality of retaining members to deliver a force to the retaining members.

In Example 40, the subject matter of Example 39 optionally includes a plurality plugs secured to the distal portion of the first plate, the plurality of plugs configured to retain the plurality of springs.

Example 41 is a failsafe for a transdermal apparatus for a prosthetic appendage, the failsafe comprising: a first plate having a central axis, the first plate comprising: a proximal portion; and a distal end opposite the proximal portion, the distal end securable with a prosthetic external to skin and configured to simulate an appendage of a patient; a second plate aligned with the central axis, the second plate comprising: a proximal end securable to a transdermal implant, the proximal end extending proximally from the second plate; and a distal portion opposite the proximal end, the distal portion configured to interface with the proximal portion of the bottom plate; and a breakaway connector coupleable within the second plate and the first plate and configured to engage the distal portion of the second plate with the proximal portion of the bottom plate, and configured to allow the second plate to break away from the first plate when a moment applied to first and second plate is larger than a threshold moment.

In Example 42, the subject matter of Example 41 optionally includes wherein the breakaway connector is secured to the second plate and is configured to break away from the bottom plate.

In Example 43, the subject matter of any one or more of Examples 41-42 optionally include a fastener passing through the breakaway connector securing the breakaway connector to the second plate.

In Example 44, the subject matter of any one or more of Examples 41-43 optionally include wherein the breakaway connector is secured to the first plate and is configured to break away from the second plate.

In Example 45, the subject matter of any one or more of Examples 41-44 optionally include an opening at the proximal end of the second plate configured to receive the transdermal implant; a collar disposed within the opening and configured to surround a distal portion of the transdermal implant; and a cam and lever coupled to the proximal end, the lever movable to actuate the cam and tighten the collar to secure the transdermal implant to the second plate.

In Example 46, the subject matter of Example 45 optionally includes a plurality of recesses in the proximal portion of the bottom plate; and a plurality of retaining members extending from the second plate and configured to engage the recesses to transfer torque between the first plate and second plate when a torque is below a threshold torque and configured to disengage from the recesses and allow rotation of the first plate relative to the second plate when the torque is above the threshold torque.

In Example 47, the subject matter of any one or more of Examples 41-46 optionally include wherein the breakaway connector is configured to cause the top plate to separator from the bottom plate due to a moment applied in any plane that is greater than the threshold moment.

In Example 48, the subject matter of any one or more of Examples 41-47 optionally include wherein the breakaway connector further comprises: a base; and a plurality of arms projecting axially from the base and extending between the second plate and the bottom plate.

In Example 49, the subject matter of Example 48 optionally includes wherein the plurality of arms each comprise a prong disposed at a termination of each arm, each prong extending radially outward from each arm.

In Example 50, the subject matter of any one or more of Examples 48-49 optionally include wherein the plurality of arms are configured to deflect radially inward, reversibly deflect and allow the second plate to break away from the bottom plate.

Example 51 is a failsafe for a transdermal apparatus for a prosthetic appendage, the failsafe comprising: a first plate comprising: a proximal portion; and a distal end opposite the proximal portion, the distal end securable with a prosthetic external to skin and configured to simulate an appendage of a patient; a second plate comprising: a proximal end securable to a transdermal implant, the proximal end extending proximally from the second plate; and a distal portion opposite the proximal end, the distal portion configured to interface with the proximal portion of the bottom plate; and a breakaway connector secured to the second plate and releasably coupled to the first plate to engage the distal portion of the second plate with the proximal portion of the bottom plate, and configured to allow the second plate to break away from the first plate when a moment applied to first and second plate is larger than a threshold moment.

In Example 52, the subject matter of Example 51 optionally includes a bore through the second plate alignable with a bore of the breakaway connector; and a fastener extending through the bore of the second plate and the bore of the breakaway connector to secure the breakaway connector to the second plate.

In Example 53, the subject matter of any one or more of Examples 51-52 optionally include wherein the first plate further comprises: a plurality of bores configured to align with a plurality of external prosthetic bores.

In Example 54, the subject matter of any one or more of Examples 51-53 optionally include wherein the first plate further comprises: a second plate central bore; and a first plate central bore aligned with the second plate central bore, the first plate central bore including a coaxial counterbore.

In Example 55, the subject matter of Example 54 optionally includes wherein the breakaway connector is secured within the second plate central bore and engages a radial surface of the coaxial counterbore to couple the second plate to the bottom plate.

Example 56 is a failsafe for a transdermal apparatus for a prosthetic appendage, the failsafe comprising: a first plate comprising: a proximal portion; and a distal end opposite the proximal portion, the distal end securable with a prosthetic external to skin and configured to simulate an appendage of a patient; a second plate comprising: a proximal end securable to a transdermal implant, the proximal end extending proximally from the second plate; and a distal portion opposite the proximal end, the distal portion configured to interface with the proximal portion of the bottom plate; and a breakaway connector secured to the first plate and releasably coupled to the second plate to engage the distal portion of the second plate with the proximal portion of the bottom plate, and configured to allow the second plate to break away from the first plate when a moment applied to first and second plate is larger than a threshold moment.

In Example 57, the subject matter of Example 56 optionally includes a hand knob threadably coupled to the breakaway connector.

In Example 58, the subject matter of Example 57 optionally includes wherein the first plate further comprises: a first plate central bore; and a second plate central bore aligned with the first plate central bore, the second plate central bore including a coaxial counterbore.

In Example 59, the subject matter of Example 58 optionally includes wherein the hand knob is configured to draw the breakaway connector toward the hand knob to engage a radial surface of the coaxial counterbore and secure the second plate to the bottom plate.

In Example 60, the subject matter of any one or more of Examples 56-59 optionally include wherein the hand knob further comprises: a threaded extension, extending proximally from the hand knob and configured to extend into the top plate to threadably engage the breakaway connector.

In Example 61, the apparatuses or method of any one or any combination of Examples 1-60 can optionally be configured such that all elements or options recited are available to use or select from.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

This disclosure relates generally to prostheses simulating appendages. A typical prosthetic may include an external prosthetic, such as a prosthetic limb, an implant, and a failsafe. The implant may include a transdermal component that can extend through the skin of the patient for connecting to a prosthetic limb or appendage.

High-level amputations (amputations near a pelvis) can create difficulties with conventional socket prosthetics. This can be because short residual limbs can have reduced mechanical advantage, resulting in many residual medical issues. The inventors have recognized, among other things, problems with high-level amputations can be addressed using a system that includes a failsafe to limit transmission of force, torque, and moments to an appendage or implant, in the event of, for example, a fall.

As used herein, the terms "proximal" and "distal" should be given their generally understood anatomical interpretation. The term "proximal" refers to a direction generally toward the torso of a patient, and "distal" refers to the opposite direction of proximal, i.e., away from the torso of a patient. It should be understood that the use of the terms "proximal" and "distal" should be interpreted as though the patient were standing with the knee joint in extension despite the apparatuses described herein generally being used with the knee joint in flexion. The intent is to differentiate the terms "proximal" and "distal" from the terms "anterior" and "posterior". As used herein, the terms "anterior" and "posterior" should be given their generally understood anatomical interpretation. Thus, "posterior" refers to a rear of the patient, e.g., a back of the knee. Similarly, "anterior" refers to a front of the patient, e.g., a front of the knee. Thus, "posterior" refers to the opposite direction of "anterior".

Figure 1:
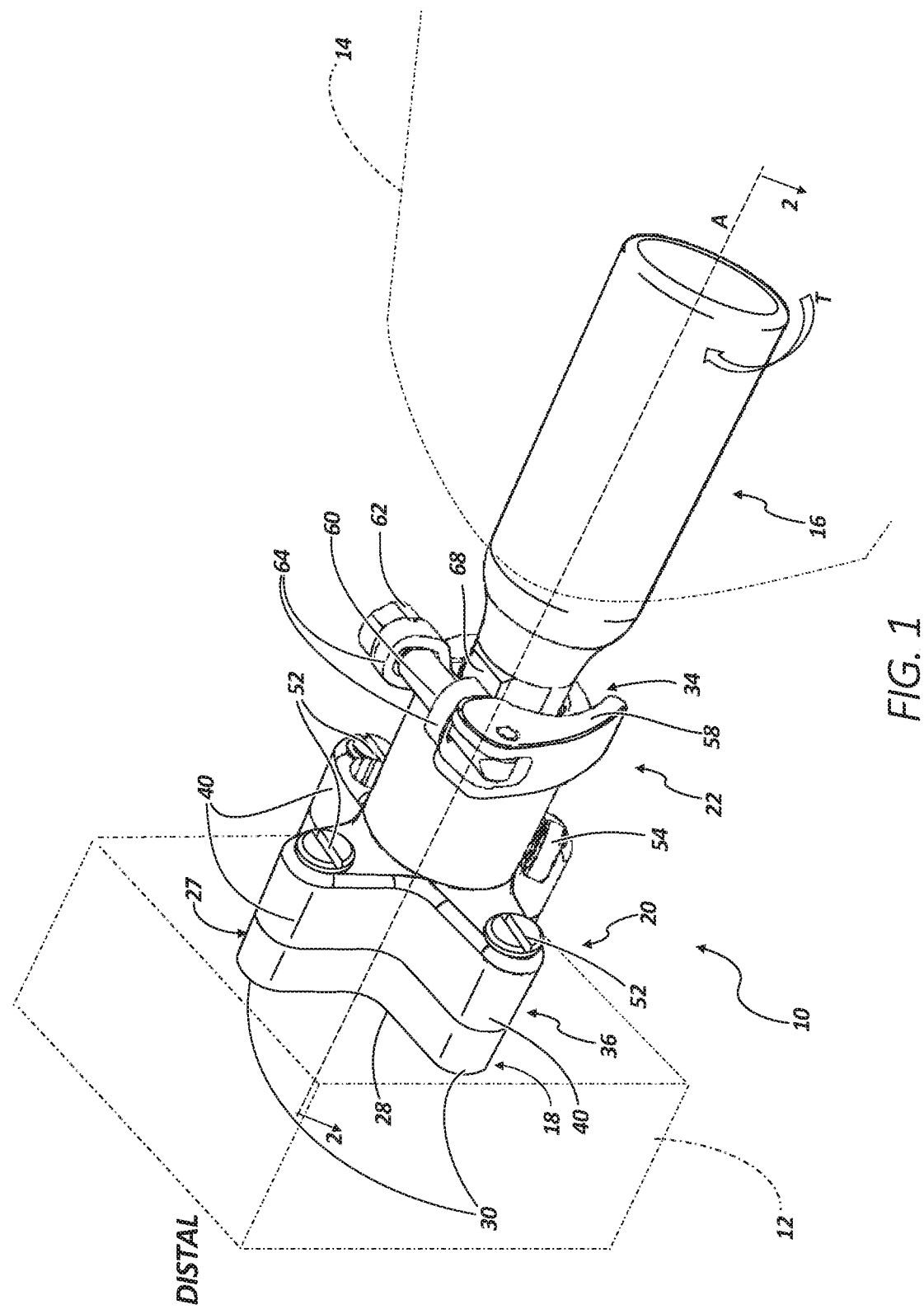
FIG. 1 shows an isometric view of a failsafe for a prosthetic limb, in accordance with an example of the present invention.
Figure 2:
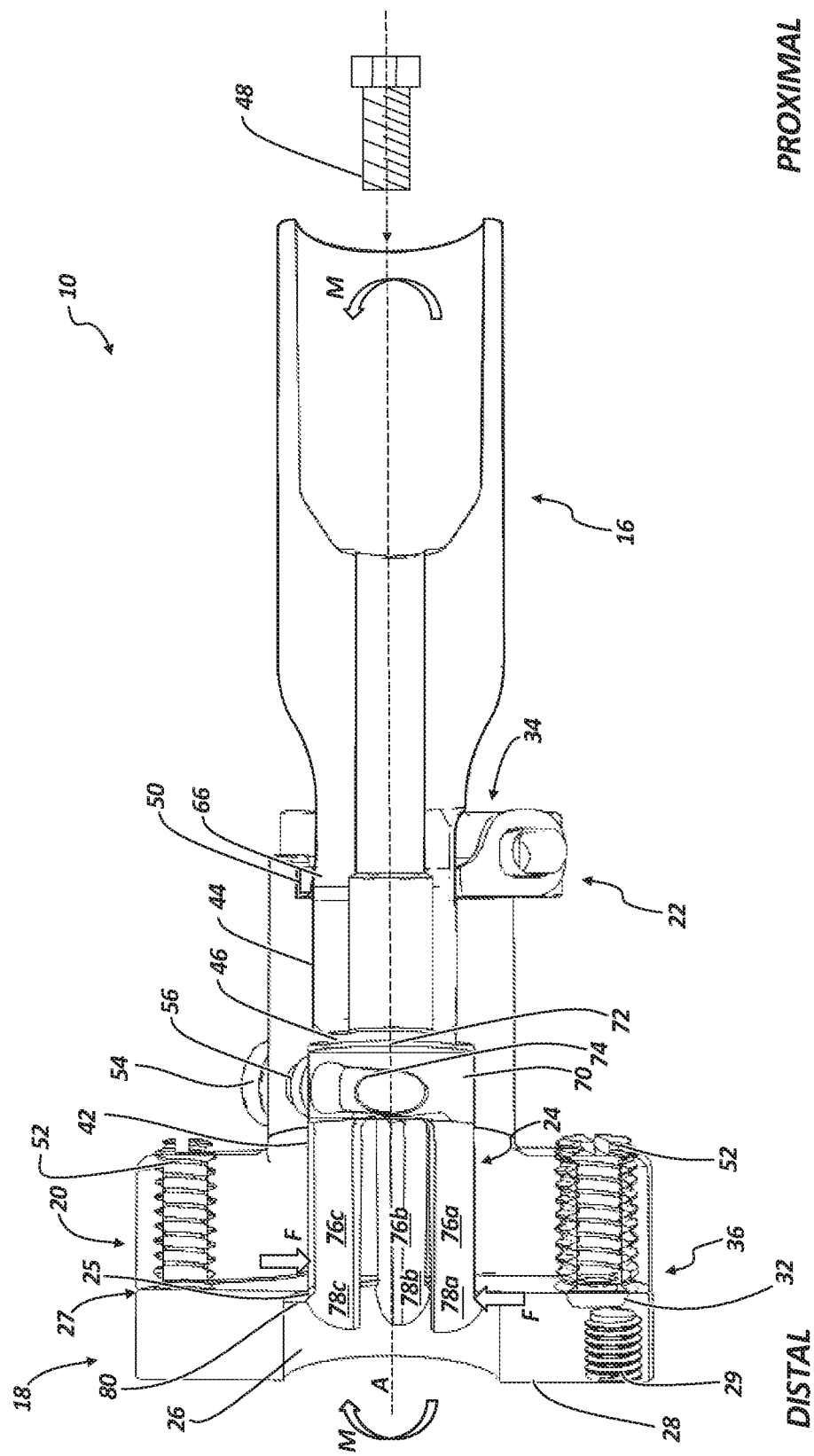
FIG. 2 shows a cross-sectional view of a failsafe for a prosthetic limb along indicators 2-2 of FIG. 1, in accordance with an example of the present invention.

FIG. 1 shows an isometric view of failsafe 10 connected to prosthetic 12 and appendage 14 via transdermal 16. FIG. 2 shows a cross-sectional view of failsafe 10 along section 2-2 of FIG. 1, in accordance with an example of the present invention. FIGS. 1 and 2 are discussed concurrently.

Failsafe 10 can include first plate (bottom plate) 18, second plate (top plate) 20, coupler 22, and breakaway connector 24. Bottom plate 18 can include central bore 25 (FIG. 2), counterbore 26 (FIG. 2), proximal portion 27, distal end 28, and prosthetic bores 29 (FIG. 2, only one visible), wings 30 (FIG. 1), and recesses 32 (FIG. 2, only one visible). Top plate 20 can include proximal end 34, distal portion 36, wings 40 (FIG. 1), central bore 42 (FIG. 2), proximal bore 44 (FIG. 2), separation plate 46 (FIG. 2), bolt 48 (FIG. 2), collar groove 50, detents 52, pin 54, and pin bore 56. Coupler 22 can include lever 58 (FIG. 1), cam 60, nut 62, and collar 64. Transdermal implant 16 can include neck portion 66 (FIG. 2) and flat 68. Breakaway connector 24 can include base 70, base bore 72, through-hole 74, arms 76a, 76b, 76c, 76d, 76e, and 76f (only arms 76a, 76b, and 76c are visible in FIG. 2), and prongs 78a, 78b, 78c, 78d, 78e, and 78f (only prongs 78a, 78b, and 78c are visible in FIG. 2). Counterbore 26 can include radial surface 80 (FIG. 2). Also shown in FIGS. 1 and 2 are orientation indicators Proximal and Distal, axis A, and forces F.

In some examples, bottom plate 18 and top plate 20 can be rigid bodies, configured to be coupled by breakaway connector 24. Bottom plate 18 and top plate 20 can be comprised of metal alloys such as steel alloys, titanium alloys, and cobalt alloys, or non-metallics, such as polymers. Bottom plate 18 can be coupled to prosthetic 12 and top plate 20 can be coupled to transdermal implant 16, which can be further connected to bone of a patient. Breakaway connector 24 can couple bottom plate 18 and top plate 20, such that breakaway connector 24 can allow top plate 20 to break away from bottom plate 18 when a bending moment, such as moment M, applied to failsafe 10 creates a force, such as forces F of FIG. 2, applied to breakaway connector 24 that is larger than a threshold force. The threshold forces or bending moment can be selected so that they are smaller than a bending moment or force that would cause failure or damage to the transdermal implant or any component within appendage 14. Because, in some examples, top plate 20 can break away from bottom plate 18 due to a bending moment in any plane, failsafe 10 can protect transdermal implant 16 and other components within appendage 14, and appendage 14 itself, from damage caused by forces in an infinite number of directions. Further, top plate 20 and bottom plate 18 can include torsion protection, through detents 52 that allows transmission of torque, such as torque T of FIG. 1, between bottom plate 18 and top plate 20, but allows top plate 20 to rotate relative to bottom plate 18 when a threshold torque is reached. Details are discussed further below.

Central bore 25 (FIG. 2) can be an annular bore through the center of bottom plate 18 that can be coaxial with axis A, which can be a central axis of top plate 20 and bottom plate 18. Counterbore 26 can also be an annular bore in bottom plate 18 that is coaxial with axis A and central bore 25, where counterbore 26 extends from distal end 28 into bottom plate 18. Counterbore 26 can have a diameter that is slightly larger than central bore 25, creating radial surface 80 that extends radially between central bore 25 and counterbore 26.

Proximal portion 27 can be disposed at a proximal side of bottom plate 18, where bottom plate 18 can engage top plate 20, as discussed further below. Distal end 28 can be disposed at a distal end of bottom plate 18, opposite proximal portion 27, and can include prosthetic bores 29 (FIG. 2, only one visible). Prosthetic bores 29 can be sized to receive a fastener in some examples. For example, prosthetic bores 29 can be sized to receive a threaded fastener that is configured to engage a common size fastener for prosthetic limbs, such as prosthetic 12.

Wings 30 (FIG. 1) can extend radially from the center of bottom plate 18, giving bottom plate 18 an X-like shape from a distal or proximal perspective. In some examples, there can be four of wings 30. In some other examples, wings 30 can have a quantity of 2, 3, 5, 6, and the like. Each of wings 30 can include recesses 32 (FIG. 2, only one visible), which can be a negative geometry in proximal portion 27, such as a proximal face of bottom plate 18.

Proximal end 34 of top plate 20 can be disposed opposite of distal portion 36. Distal portion 36 can be configured to engage proximal portion 27 of bottom plate 18. In some examples, distal portion 36 and proximal portion 27 can include flat surfaces substantially orthogonal to axis A, where the flat (or planar) surfaces can be configured to mate. Distal portion 36 and proximal portion 27 can have other shapes in some other examples that are configured to engage or mate.

Wings 40 (FIG. 1) can extend radially from the center of top plate 20, giving top plate 20 an X-like shape from a distal or proximal perspective. In some examples, there can be four of wings 40. In some other examples, wings 30 can have a quantity of 2, 3, 5, 6, and the like. Each of wings 40 can include a bore configured to receive detents 52. Detents 52 can be a threaded detent, similar to a screw or bolt and having a distal termination configured to engage recesses 32, as described further below. Each of detents 52 can be independently adjustable.

Central bore 42 (FIG. 2) of top plate 120 can be coaxial with central bore 25 of bottom plate 28 and central bores 42 and 25 can also be of the same diameter, such that when top plate 20 and bottom plate 18 engage, central bores 25 and 42 align.

Proximal bore 44 (FIG. 2) can also be coaxial with central bores 25 and 42; however, proximal bore 44 can have a diameter that is of a different size, such as larger or smaller (as shown in the example of FIG. 2). Proximal bore 44 can extend substantially through a proximal portion of top plate 20 and extend entirely through proximal end 34, creating an annular opening at proximal end 34. Proximal bore 44 can be separated from central bore 42 by separation plate 46 (FIG. 2). Separation plate 46 can have a small thickness in the axial direction, to help reduce the axial length of top plate 20.

In some examples, pin 54 can be configured to pass through pin bore 56 of top plate 20 and through through-hole 74 of breakaway connector 24 to secure breakaway connector 24 to top plate 20. In other examples, pin 54 can threadably engage pin bore 56 and through-hole 74 to secure breakaway connector to top plate 20.

In some other examples, bolt 48 (FIG. 2) can be inserted into proximal bore 44 to threadably engage breakaway connector 24, such that bolt 48 secures breakaway connector 24 to separation plate 46. This example can have the benefit of reducing tolerance stack (or slop), by reducing axial gaps between the components of failsafe 10.

Coupler 22 can be externally coupled to top plate 20 at proximal end 34. Collar groove 50 can be a groove, or a larger diameter bore, in proximal bore 44. Collar groove 50 can be sized to retain collar 64 so that collar 64 is aligned with proximal bore 44.

Collar 64 can be a spring collar or clamp, configured to secure a member through friction. Cam 60 can pass through two eyes of collar 64 and can be secured at one end to nut 62 and at an opposite end to lever 58. Lever 58 can be actuated by a user, or patient, between an open and closed position. When actuated from an open to a closed position, lever 58 can rotate to contact an eye of collar 64 and draw cam 60 and nut 62 closer to lever 58, causing nut 62 to contact the other eye, and causing the two eyes of collar 64 to come together, reducing a diameter of collar 64. In operation of some examples, transdermal implant 16 can be inserted into top plate 20 through proximal end 34 and into proximal bore 44, where transdermal implant 16 is surrounded by collar 64. Then, a user can actuate lever 58 to a closed position to tighten or close collar 64 to secure transdermal implant 16 to top plate 20. In some examples, nut 62 can adjust the effective length of cam 60, allowing the force applied by collar 64 to be adjusted.

Transdermal implant 16 can include neck portion 66 (FIG. 2) which can be a flare having a reduced diameter for engagement of collar 64 further securing transdermal implant to top plate 20. Flat 68 can be a flat portion of transdermal implant 16 configured to aid in alignment of transdermal implant 16 with top plate 20, as discussed further below.

Breakaway connector 24 can be a central cantilevered spring, in some examples, comprised of a material having an elastic deformation range suitable to deflect as described herein without deforming. In some examples, breakaway connector can be comprised of steel alloys, titanium alloys, and cobalt alloys. In some examples, breakaway connector can be comprised of a titanium alloy such as Ti-6Al-4V. As discussed above, breakaway connector 24 can include base 70, which can include a base bore 72. Base bore 72 can be threaded to receive bolt 48 to secure breakaway connector 24 to top plate 20. Breakaway connector can also be secured to top plate 20 by a pin through through-hole 74, as discussed above.

Breakaway connector 24 can have a generally cylindrical shape in some examples and can have other geometric shapes, such as a hexagonal prism, in other examples. Base 70 can be a cylindrical portion of breakaway connector 24 at the proximal end of breakaway connector, where arms 76a, 76b, 76c, 76d, 76e, and 76f (only arms 76a, 76b, and 76c are visible in FIG. 2) can extend axially is a distal direction from base 70. Proximate terminations of arms 76a-76f, arms 76a-76f can include prongs 78a, 78b, 78c, 78d, 78e, and 78f (only prongs 78a, 78b, and 78c are visible in FIG. 2). Prongs 78a-78f can be radial extensions of arms 76a-76f, respectively, having a radial surface on a proximal termination of each of prongs 78a-78f that is configured to engage radial surface 80 of counterbore 26.

In assembly of one example, breakaway connector 24 can be inserted through central bore 42 of top plate 20 so that base 70 abuts separation plate 46. Breakaway connector 24 can then be secured to top plate 20 using pin 54 in one example, or bolt 48 in another example. Bottom plate 18 can be secured to breakaway connector 24 and top plate 20 by engaging central bore 25 with prongs 78a-78f of breakaway connector 24. When engaged, central bore 25 can force prongs 78a-78f, and therefore arms 76a-76f, to deflect radially inward. Arms 76a-76f will elastically deform (or reversibly deflect) as proximal portion 27 engages distal portion 36. Once prongs 78a-78f reach counterbore 26, arms 76a-76f can expand (or deflect radially outward) to their natural shape. Thereafter, prongs 78a-78f can engage radial surface 80 of counterbore 26, which can prevent separation of top plate 20 from bottom plate 18.

Top plate 20 can also connect to transdermal implant 16, as described above, where transdermal implant 16 is inserted into proximal bore 44 to engage separation plate 46. And, lever 58 of coupler 22 can be actuated to a closed position such that collar 64 engages necked portion 66 of transdermal implant 16 to prevent axial movement in a proximal direction of transdermal implant 16, while separation plate 46 prevents transdermal implant from moving axially a distal direction.

Bottom plate 18 can also be connected to a prosthetic appendage, such as prosthetic 12 of FIG. 1 using prosthetic bores 29. After assembly is complete, failsafe 10 can couple an appendage, such as appendage 14 of FIG. 1, to a prosthetic, such as prosthetic 12 of FIG. 1, while providing failsafe operation to protect transdermal implant 16, appendage 14, and other body parts of a patient from damage caused by forces transferred from prosthetic 12 to appendage 14 and from appendage 14 to prosthetic 12.

In operation of some examples, a user (or patient) can use failsafe 10 to secure prosthetic 12 to appendage 14, as described above. During operation of failsafe 10, failsafe 10 can transmit forces and bending moments between appendage 14 and prosthetic 12 to enable a user to perform movements such as running, walking, jumping, and the like. In some instances of performing movements, a user may apply a compressive axial force to failsafe 10 with or without a bending moment. Between movements, a tensile axial force may be applied to failsafe 10 along with or without a bending moment, for example, when prosthetic 12 is raised off a floor or ground surface. Failsafe 10 can be designed to allow transmission of forces and moments between appendage 14 and prosthetic 12 when the forces and moments are within an allowable or expected range, enabling the use of prosthetic 12 for everyday activities. Failsafe 10 can also be configured so that a force or moment, such as moment M of FIG. 2, that is larger than a threshold moment causes top plate 20 to separate from bottom plate 18. The threshold moment can be selected to be lower than a moment that could cause damage to any one of prosthetic 12, appendage 14, implant 16, or any component or part within appendage 14.

More specifically, pure compressive forces applied to failsafe 10 along axis A can be transferred between appendage 14 and prosthetic 12. Forces applied to failsafe 10 by appendage 14 or prosthetic 12 that are not coaxial with axis A may create a moment, such as moment M, that creates a sheer force between top plate 20 and bottom plate 18. Failsafe 10 can transfer forces and therefore bending moments between appendage 14 and prosthetic 12 through bottom plate 18, top plate 20, breakaway connector and transdermal implant. When a force creates a bending moment applied to failsafe 10, the moment is transferred to breakaway connector 24 by bottom plate 18 and top plate 20 through forces F. The bending moment, such as moment M, will be applied to arms 76a-76f and/or prongs 78a-78f. Once moments M become larger than a threshold moment, forces F can cause arms 76a-76f to deflect far enough so that prongs 78a-78b disengage from radial surface 80 and decrease in diameter to fit within central bores 25 and 42. Because breakaway connector 24 couples bottom plate 18 to top plate 20, when breakaway connector 24 disengages radial surface 80 and enters central bores 25 and 42, top plate 20 can separate from bottom plate 18 due to any axial tensile force, such as a force applied due to gravity from the mass of prosthetic 12. This breakaway action can prevent the transmission of potentially damaging forces and moments to transdermal implant 16 and appendage 14, which can save cost and improve quality of life for a patient.

During operation, top plate 20 and bottom plate 18 may be entirely separate. In such cases, bolt 48 in one example, and pin 54 in another example, can retain breakaway connector 24 within top plate 20, to prevent damage or loss of breakaway connector 24.

Failsafe 10 can also provide torsion protection. In operation of some examples, torque T can be applied to top plate 20 or bottom plate 18 along axis A. Top plate 20 and bottom plate 18 can be configured to transfer torque T, allowing torsion up to a threshold torsion. Specifically, detents 52 can engage recesses 32 to transfer torsion between bottom plate 18 and top plate 20 and prevent relative rotation of top plate 20 to bottom plate 18. When a threshold torsion is reached, detents 52 can release from recesses 32, allowing top plate 20 to rotate relative to bottom plate 18. This can provide the benefit of preventing transmission of damaging torque to appendage 14 and components within appendage 14, such as an implant. Because torsion protection is mechanically independent from moment protection, the threshold torque can be adjusted separately from the threshold moment, offering customization of failsafe 10. Further, because top plate 20 does not break away from bottom plate 18 when a threshold torque is met and top plate 20 and bottom plate 18 rotate, the plates can be quickly reset relative to one another to realign the prosthetic.

Figures 3A, 3B:
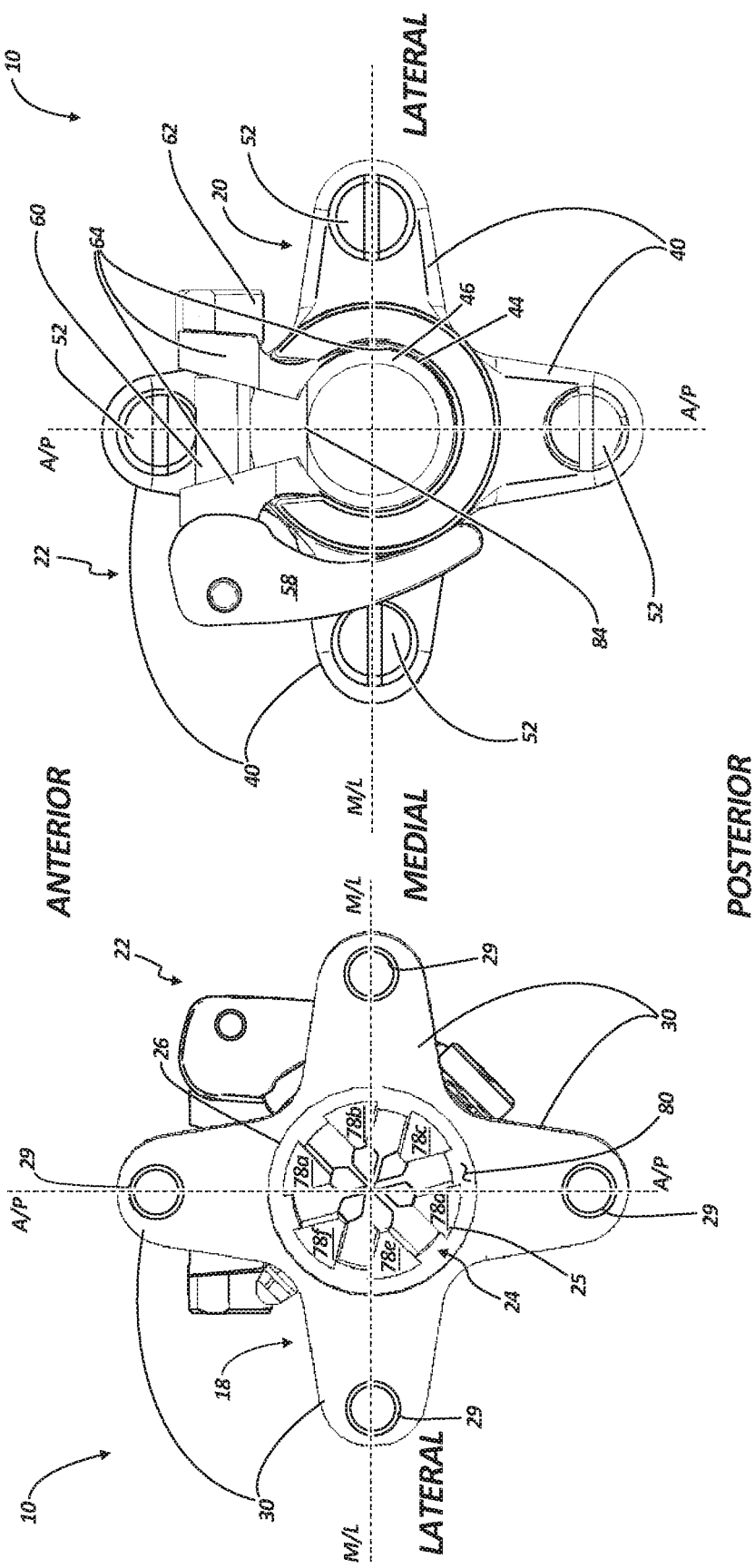
FIG. 3A shows an end view of a failsafe from a distal perspective, in accordance with an example of the present invention.
FIG. 3B shows an end view of a failsafe from a proximal perspective, in accordance with an example of the present invention.

FIG. 3A shows an end view of failsafe 10 from a distal perspective. FIG. 3B shows an end view of failsafe 10 from a proximal perspective. FIGS. 3A and 3B are discussed concurrently. Failsafe 10 can include bottom plate 18, top plate 20, connector 22, and breakaway connector 24. Bottom plate 18 can include central bore 25, counterbore 26, prosthetic bores 29, wings 30, and radial surface 80. Top plate 20 can include wings 40, proximal bore 44, separation plate 46, and detents 52. Proximal bore can include internal flat 84. Coupler 22 can include lever 58, cam 60, nut 62, and collar 64. Breakaway connector 24 can include prongs 78a-78f (FIG. 3A). Transdermal 16 is not shown in FIGS. 3A and 3B to more clearly show the components of coupler 22. Also shown in FIGS. 3A and 3B are reference indicators Anterior and Posterior, anterior/posterior plane (A/P), and medial/lateral plane (M/L).

The components of failsafe 10 shown in FIGS. 3A and 3B connect and operate consistently with the components of failsafe 10 of FIGS. 1 and 2. However, FIGS. 3A and 3B show additional detail of some components.

FIG. 3A shows prosthetic bores 29 each disposed on each of wings 30. In some example, prosthetic bores 29 do not extend entirely through bottom plate 18, as prosthetic bores 29 align with recesses 32. In some examples, prosthetic bores 29 can be arranged in a four-bolt pattern that is common to external prosthetic limbs.

FIG. 3A also shows prongs 78a-78b disposed around central bore 25 and engaging radial surface 80 of counterbore 60. Prongs 78a-78b are shown as being equally circumferentially spaced, but can be asymmetrically spaced in some examples. Prongs 78a-78f can have a substantially triangular profile in some examples, and can have other geometric profiles in other examples.

FIG. 3B shows detents 52 each disposed on each of wings 40. Detents 52 can include a head that is configured to receive a tool, such as a standard or flat head screwdriver (as shown in FIG. 3B), and can be configured to receive other tools, such as hex, cross-recess, star-shaped, and the like.

FIG. 3B also shows collar 64 within proximal bore 44 and disposed in collar groove 50 (of FIG. 2). FIG. 3B further shows internal flat 84, which can be a flat portion of internal bore 44. Internal flat 84 can be used to align transdermal implant 16 with internal bore 44. In some examples, internal flat 84 can be sized so that flat 68 must be aligned with internal flat 84 for transdermal implant 16 to be inserted into internal bore 44. In some examples, this alignment feature can be used to align wings 30 and 40 of bottom plate 18 and top plate 20, respectively, with the anterior/posterior plane and medial/lateral plane, as shown in FIGS. 3A and 3B.

Top plate 20 and bottom plate 18 can save weight by using a winged geometry (wings 40 and 30, respectively), over other geometric shapes, such as a cylinder or rectangular prism, also including prosthetic bores configured to mate with common prosthetic bolt patterns.

In operation of some examples, due to their geometry, wings 30 and 40 can affect a bending moment transferred through failsafe 10. For example, the bending moment required to break top plate 20 away from bottom plate 20 is largest along the medial/lateral plane and the anterior posterior plane. This can have the benefit of limiting bending moments along a plane where the moments are more likely to occur. In some examples, flat 68 and internal flat 84 can be used to ensure that wings 30 and 40 align with the medial/lateral plane and the anterior/posterior plane.

Figure 4:
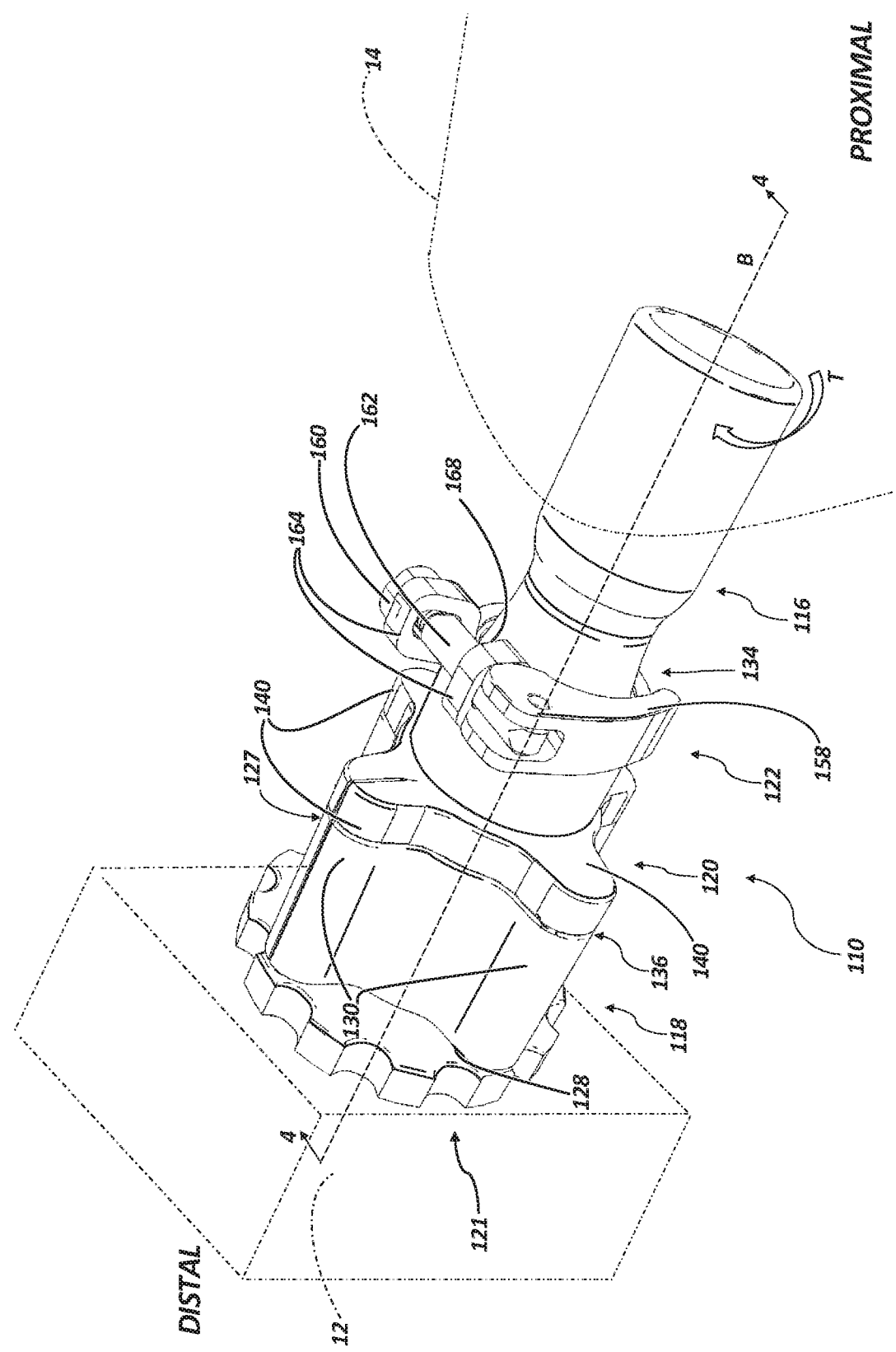
FIG. 4 shows an isometric view of a failsafe for a prosthetic limb, in accordance with a second example of the present invention.
Figure 5:
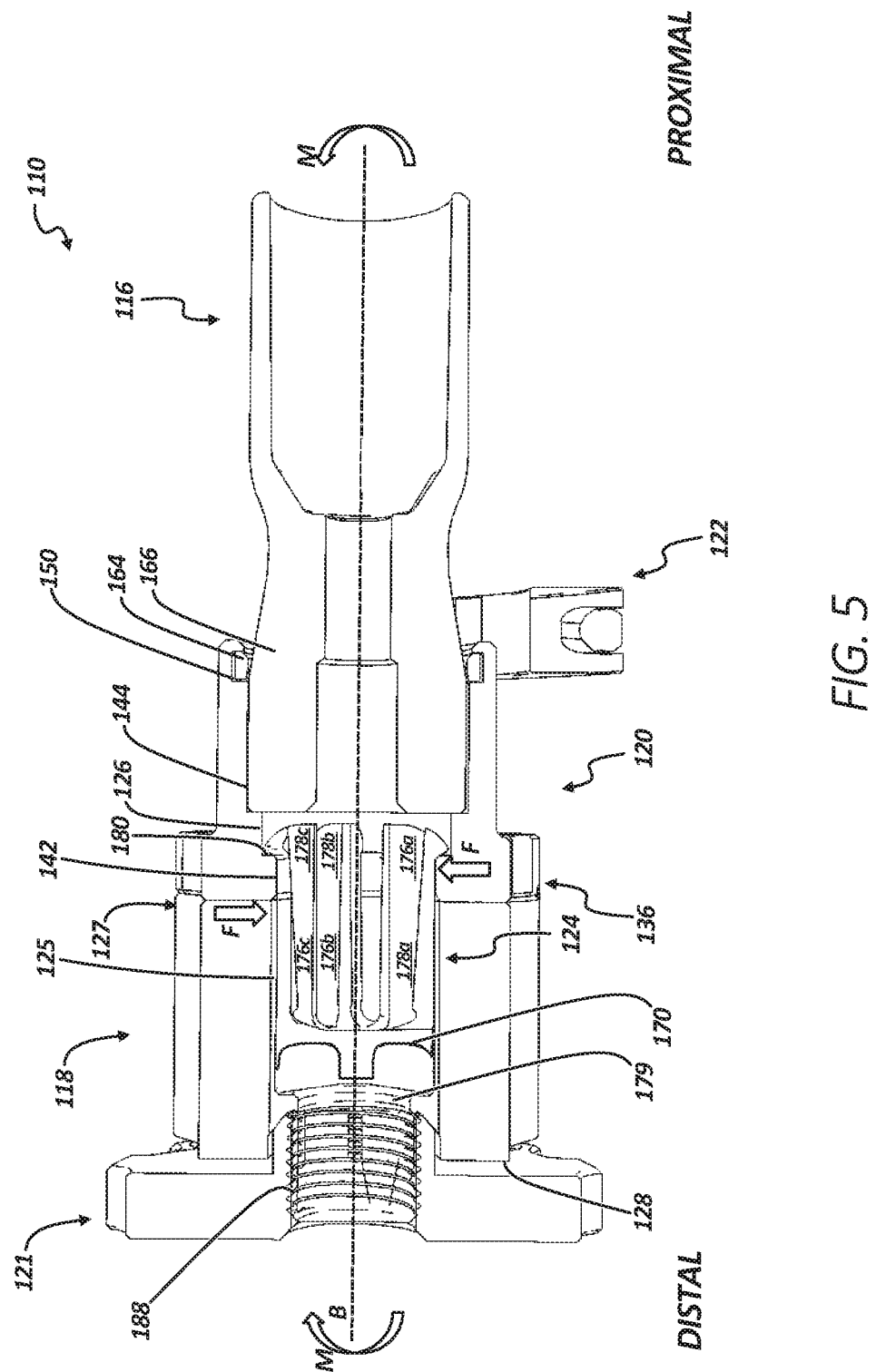
FIG. 5 shows a cross-sectional view of a failsafe for a prosthetic limb along indicators 5-5 of FIG. 4, in accordance with an example of the present invention.

FIG. 4 shows an isometric view of failsafe 110 connected to prosthetic 12 and appendage 14 via transdermal 116. FIG. 5 shows a cross-sectional view of failsafe 110 along section 4-4 of FIG. 4, in accordance with an example of the present invention. FIGS. 4 and 5 are discussed concurrently.

Failsafe 110 can include first plate (bottom plate) 118, second plate (top plate) 120, hand knob 121, coupler 122, and breakaway connector 124. Bottom plate 118 can include central bore 125 (FIG. 5), proximal portion 127, distal end 128, and wings 30 (FIG. 4). Top plate 20 can include proximal end 134, distal portion 136, wings 140 (FIG. 4), central bore 142 (FIG. 5), counterbore 126 (FIG. 5), proximal bore 144 (FIG. 5), and collar groove 150. Coupler 122 can include lever 158 (FIG. 4), cam 160, nut 162, and collar 164. Transdermal implant 116 can include neck portion 166 (FIG. 5) and flat 168 (FIG. 5). Breakaway connector 124 can include base 170, arms 176a, 176b, 176c, 176d, 176e, and 176f (only arms 176a, 176b, and 176c are visible in FIG. 5), prongs 178a, 178b, 178c, 178d, 178e, and 178f (only arms 176a, 176b, and 176c are visible in FIG. 5), and threaded portion 179. Counterbore 126 can include radial surface 180 (FIG. 5). Hand knob 121 can include threaded extension 188. Also shown in FIGS. 3 and 4 are orientation indicators Proximal and Distal, axis B, moments M, and forces F.

The components of failsafe 110 can be similar to failsafe 10, except that failsafe 110 can include hand knob 121 to secure breakaway connector 124 to knob 121, bottom plate 118, and top plate 120. Hand knob 121 can be operated by hand (without tools) to install or set up failsafe 110. This can allow a user or patient to quickly connect or reconnect the components of failsafe 110.

Coupler 122 and transdermal implant 116 can be connected and operate consistently with coupler 22 and transdermal implant 16, respectively, as described in FIGS. 1-3B above.

In some examples, bottom plate 118 and top plate 120 can be rigid bodies, configured to be coupled by breakaway connector 124. Bottom plate 118 can be coupled to prosthetic 12 and top plate 120 can be coupled to transdermal implant 16, which can further be connected to bone of a patient. Breakaway connector 124 can couple to handle 121, bottom plate 118, and top plate 120, such that breakaway connector 124 can allow top plate 120 to break away from bottom plate 118 when a bending moment applied to failsafe 110 creates a force, such as forces F of FIG. 5, applied to breakaway connector 124 that are larger than a threshold force. The threshold forces or bending moment can be selected so that they are smaller than a bending moment or force that would cause failure or damage to transdermal implant 116 or any component within appendage 14. Because, in some examples, top plate 120 can break away from bottom plate 118 due to a bending moment from any direction about axis A, failsafe 110 can protect transdermal implant 116 and other components within appendage 14, and appendage 14 itself, from damage caused by forces from an infinite number of directions. Details are discussed further below.

Central bore 125 (FIG. 5) can be an annular bore through the center of bottom plate 18 coaxial with axis A, which can be a central axis of top plate 20 and bottom plate 18.

Proximal portion 27 can be at a proximal side of bottom plate 18, where bottom plate 118 can engage top plate 120, as discussed further below. Distal end 128 can be disposed at a distal end of bottom plate 118, opposite proximal portion 127.

Wings 130 (FIG. 4) can extend radially from the center of bottom plate 118, giving bottom plate 118 an X-like shape from a distal or proximal perspective. In some examples, there can be four of wings 130. In some other examples, wings 130 can have a quantity of 2, 3, 5, 6, and the like.

Proximal end 134 of top plate can be disposed opposite of distal portion 136. Distal portion 136 can be configured to engage proximal portion 127 of bottom plate 118. In some examples, distal portion 136 and proximal portion 127 can include flat surfaces orthogonal to axis B, where the flat (or planar) surfaces can be configured to mate. Distal portion 136 and proximal portion 127 can have other shapes in some other examples that are configured to engage or mate.

Wings 140 (FIG. 4) can extend radially from the center of top plate 120, giving top plate 120 an X-like shape from a distal or proximal perspective. In some examples, there can be four of wings 140. In some other examples, wings 140 can have a quantity of 2, 3, 5, 6, and the like. Each of wings 140 can include a bore configured to receive detents, as discussed further below.

Central bore 142 (FIG. 5) of top plate 120 can be coaxial with central bore 125 of bottom plate 118 and central bores 142 and 125 can also be of the same diameter, such that when top plate 120 and bottom plate 118 engage, central bores 125 and 142 align.

Counterbore 126 can also be an annular bore within top plate 120 that is coaxial with axis B and central bore 142. Counterbore 126 can have a diameter that is slightly larger than central bore 142, creating radial surface 180 that extends radially between central bore 142 and counterbore 126.

Proximal bore 144 (FIG. 5) can also be coaxial with central bores 125 and 142; however, proximal bore 144 can have a diameter that is of a different size, such as larger or smaller (as shown in the example of FIG. 5) diameter. Proximal bore 144 can extend substantially through a proximal portion of top plate 120 and extend entirely through proximal end 134, creating an annular opening at proximal end 134.

Breakaway connector 124 can have a generally cylindrical shape in some examples and can have other geometric shapes, such as a hexagonal prism, in other examples. Base 170 of breakaway connector 124 can include a threaded portion 179, which can be a female threaded portion extending distally from base 170. Base 170 can be a cylindrical portion of breakaway connector 124 at the distal end of breakaway connector, where arms 176a, 176b, 176c, 176d, 176e, and 176f (only arms 176a, 176b, and 176c are visible in FIG. 5) can extend axially is a proximal direction from base 170. Proximate terminations of arms 176a-176f can include prongs 178a, 178b, 178c, 178d, 178e, and 178f (only prongs 178a, 178b, and 178c are visible in FIG. 5). Prongs 178a-178f can be radial extensions of arms 176a-176f, respectively, having a radial surface on a distal termination of each of prongs 178a-178f that can be configured to engage radial surface 180 of counterbore 126.

Hand knob 121 can include distal and proximal sides, where the proximal side can be configured to engage distal end 128 of bottom plate 118. Threaded extension 188 can extend axially through hand knob 121 and protrude from the proximal side of hand knob 121. Threaded extension 188 can include a protrusion configured with male threading to engage threaded portion 179 of breakaway connector 124, as discussed below.

In assembly of one example, breakaway connector 124 can be inserted into proximal bore 144 with base 170 and threaded portion 179 disposed near distal end 128 within central bore 125. Then hand knob 121 can threadably couple to threaded portion 179 of breakaway connector 124 to pull prongs 178a-178f against radial surface 180 and/or central bore 142, securing hand knob 121 to bottom plate 118 and securing breakaway connector to top plate 120, which effectively can secure bottom plate 118 to top plate 120. This configuration of failsafe 110 can offer the benefit of assembly and reassembly of the components of failsafe 110 without tools, as breakaway connector 124 can be threaded into hand knob 121 by hand to secure top plate 120 to bottom plate 118.

Following a breakaway of top plate 120 from bottom plate 118, transdermal implant 116 can be disengaged from top plate 120 using coupler 122. Then, hand knob 121 can be unthreaded from breakaway connector 124. Breakaway connector 124 can then be inserted through proximal bore 144 and re-secured, as described above. Because lever 158 and hand knob 121 can be operated using hands, tools are not required for disassembly and reassembly of failsafe 110.

Figure 6B:
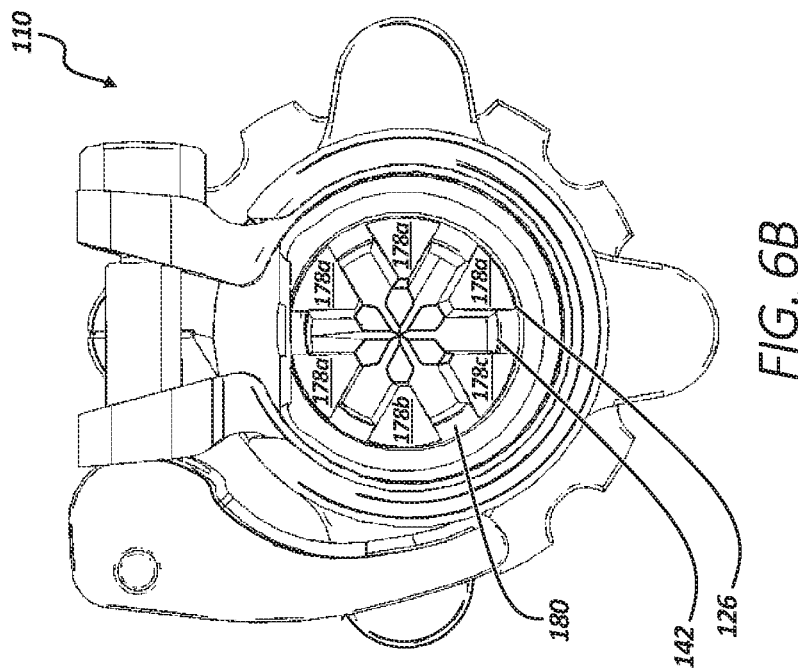
FIG. 6B shows an end view of a failsafe from a proximal perspective, in accordance with an example of the present invention.
Figure 6A:
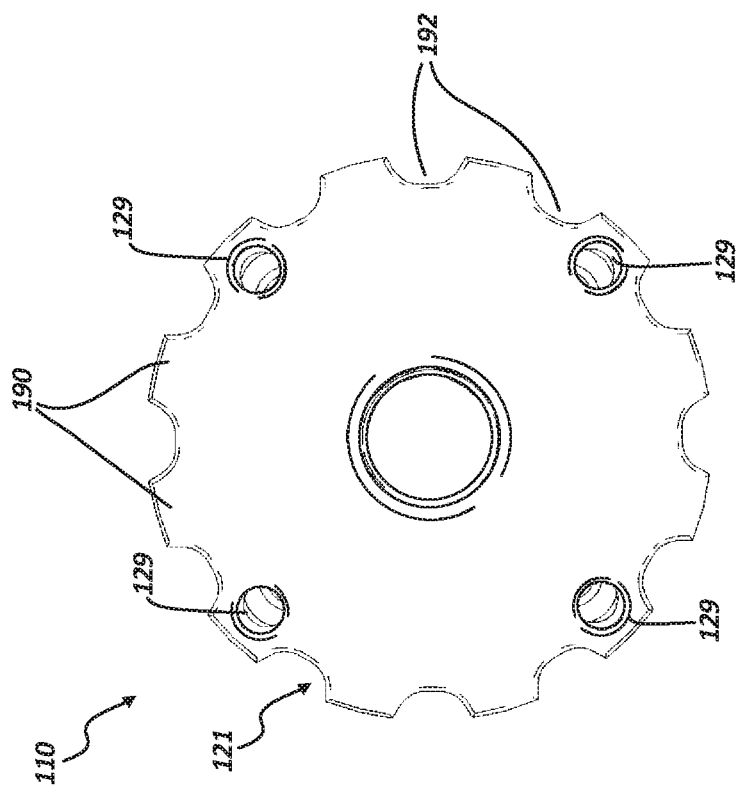
FIG. 6A shows an end view of a failsafe from a distal perspective, in accordance with an example of the present invention.

Hand knob 121 can be connected to a prosthetic appendage, such as prosthetic 12 of FIG. 4, using prosthetic bores 129 (FIG. 6A). After assembly is complete, failsafe 110 can couple an appendage, such as appendage 14 of FIG. 4 to a prosthetic, such as prosthetic 12 of FIG. 4, while providing failsafe operation to protect transdermal implant 16, appendage 14, and other body parts of a patient from damage caused by forces transferred from prosthetic 12 to appendage 14 and from appendage 14 to prosthetic 12.

Failsafe 110 can be used consistently with failsafe 10 of FIGS. 1-3B above to secure prosthetic 12 to appendage 14 prevent damage to any one of prosthetic 12, appendage 14, implant 116, or any component or part within appendage 14 by limiting forces and moments transferred between prosthetic 12 and appendage 14.

During operation, top plate 120 and bottom plate 118 may entirely separate. In such cases, hand knob 121 can retain breakaway connector 124 to prevent damage or loss of breakaway connector 124.

FIG. 6A shows an end view of failsafe 110 from a distal perspective. FIG. 6B shows an end view of failsafe 110 from a proximal perspective. FIGS. 6A and 6B are discussed concurrently. The components of failsafe 110 can be connected and can operate consistently with FIGS. 4 and 5; however, FIGS. 6A and 6B show additional details of some components of failsafe 110.

Hand knob 121 (FIG. 6A) includes prosthetic bores 129, protrusions 190, and notches 192. Prosthetic bores 129 can be used to couple to a prosthetic limb, such as prosthetic 112 of FIG. 1. Prosthetic bores 129 can be threaded bores arranged in a bolt pattern common to external prosthetics. Protrusions 190 and notches 192 can create a crenulated surface profile, which can be useful in tightening hand knob 121 in engaging with breakaway connector 124.

FIG. 6B shows how prongs 178a-178f can engage radial surface 180 created by central bore 142 and counterbore 126.

Figure 7:
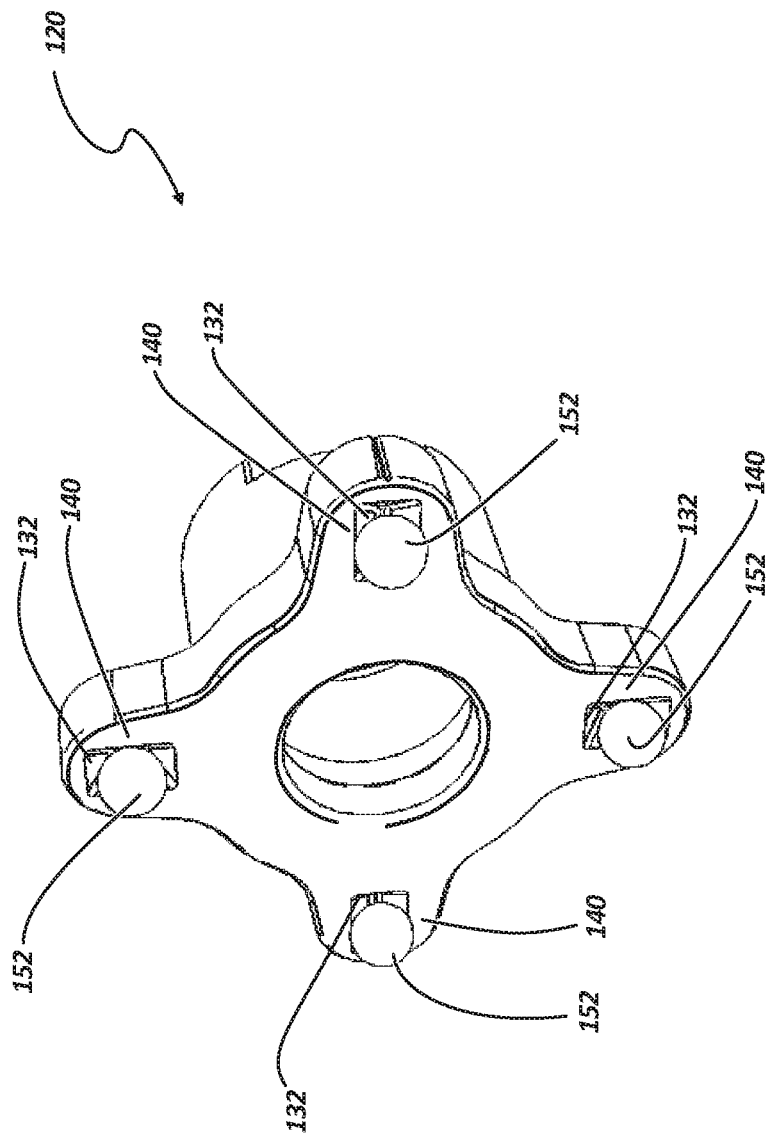
FIG. 7 shows an isometric view of a top plate and detents of a failsafe, in accordance with an example of the present invention.

FIG. 7 shows an isometric view of top plate (second plate) 120 and detents 152. Top plate 120 can include wings 140 and recesses 132.

Recesses 132 can be a negative geometry in the surface of each of wings 140 of top plate 120. Recesses 132 can be sized to receive detents 152, which can engage recesses 132 to restrict relative rotation of top plate 120 to bottom plate 118, but allowing relative rotation when a threshold rotational force is applied to either of top plate 120 or bottom plate 118. Though not shown in FIG. 7, an adjustment device, such as a compression spring, can be configured to engage detents 152 to adjust the threshold rotational force. Because the springs can be replaceable (selectable), detents 152 can be customized for a desired rotational or a desired torsional threshold.

Figure 8:
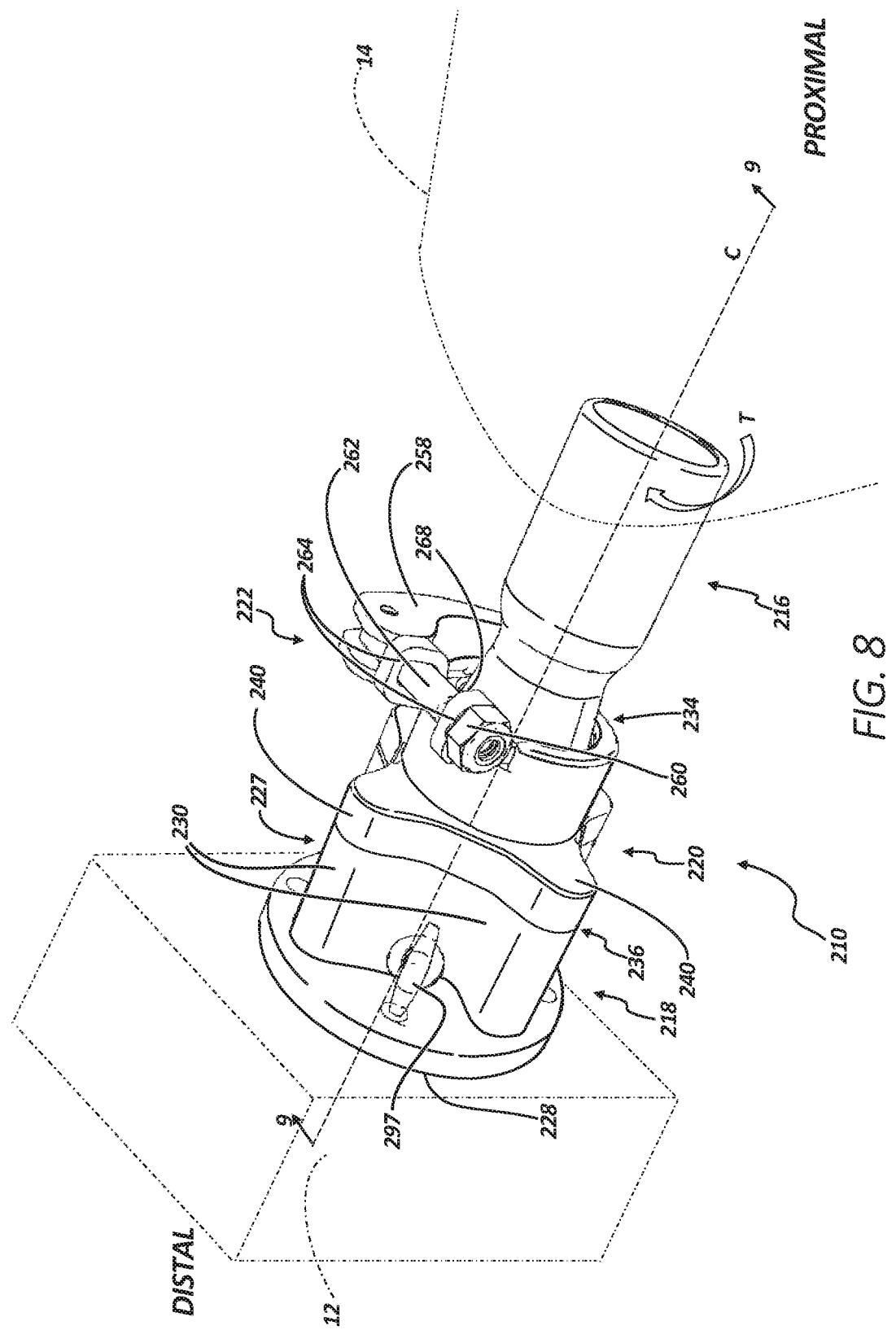
FIG. 8 shows an isometric view of a failsafe for a prosthetic limb, in accordance with an example of the present invention.
Figure 9:
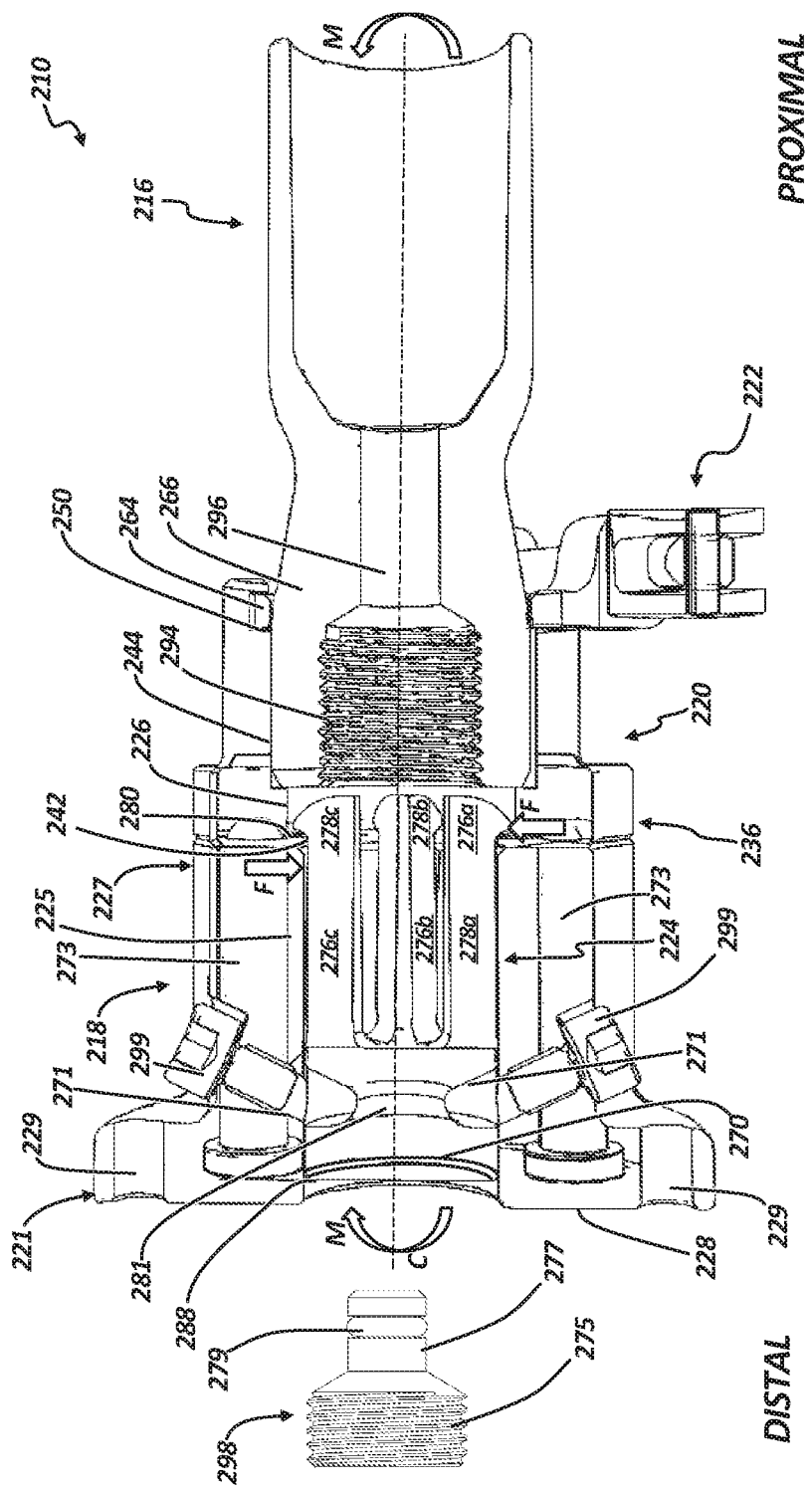
FIG. 9 shows a cross-sectional view of a failsafe for a prosthetic limb along indicators 9-9 of FIG. 8, in accordance with at least one example of the present invention.

FIG. 8 shows an isometric view of failsafe 210 connected to prosthetic 12 and appendage 14 via transdermal 216. FIG. 9 shows a cross-sectional view of failsafe 210 along indicators 9-9 of FIG. 8. FIGS. 8 and 9 are discussed below concurrently.

Failsafe 210 can include first plate (bottom plate) 218, second plate (top plate) 220, coupler 222, breakaway connector 224, breakaway retainer 297 (FIG. 8), plug 298, and retainer fasteners 299 (FIG. 9). Bottom plate 218 can include central bore 225 (FIG. 9), proximal portion 227, distal end 228, wings 230 (FIG. 8), retainer bores 271, and spring bores 273. Top plate 220 can include proximal end 234, distal portion 236, wings 240 (FIG. 8), central bore 242 (FIG. 9), counterbore 226 (FIG. 9), proximal bore 244 (FIG. 9), and collar groove 250. Coupler 222 can include lever 258 (FIG. 8), cam 260, nut 262, and collar 264. Transdermal implant 216 can include neck portion 266 (FIG. 9), flat 268, internal threaded portion 294, and sealing bore 296. Breakaway connector 224 can include base 270, arms 276a, 276b, 276c, 276d, 276e, and 276f (only arms 276a, 276b, and 276c are visible in FIG. 9), prongs 278a, 278b, 278c, 278d, 278e, and 278f (only arms 276a, 276b, and 276c are visible in FIG. 9), and recessed portion (or circumferential groove or retainer groove) 281. Counterbore 226 can include radial surface 280 (FIG. 9). Plug 298 can include threaded portion 275, sealing portion 277, and o-ring 279. Also shown in FIGS. 8 and 9 are orientation indicators Proximal and Distal, axis C, moments M, and forces F.

The components of failsafe 210 can be similar to failsafes 10 and 110, except that failsafe 210 can include plug 298, which can threadably engage internal threaded portion 294 at threaded portion 275. When plug 298 is threaded into internal threaded portion 294 of transdermal implant 216, sealing portion 277 of plug can extend into sealing bore 296 of transdermal implant 216. When sealing portion 277 is inserted into sealing bore 296, o-ring 279 can create a seal between plug 298 and transdermal implant 216.

Failsafe 210 can also differ in that failsafe 210 can include breakaway retainer 297 and retainer fasteners 299. Retainer bores 271 can be bores extending through bottom plate 218. In some examples, retainer bores 271 can include bores of a quantity of 1, 2, 3, 4, 5, 6, 8, and the like. In some examples, retainer bores 271 can extend through bottom plate at an angle relative to centerline C, where retainer bores 271 angle towards distal end 228 as retainer bores 271 extend radially inward and intersect central bore 225. In some examples, retainer bores 271 can be threaded to accept breakaway retainer 297 and/or retainer fasteners 299.

Breakaway retainer 297 can be a threaded thumb screw in some examples, and can be other types of fasteners, such as bolt or pin, in other examples. In some examples, breakaway retainer 297 can threadably engage any of retainer bores 271 to extend through bottom plate at an angle relative to centerline C, where breakaway retainer 297 angles distally and radially inward toward centerline C and toward retainer groove 281. Breakaway retainer 297 can engage breakaway connector 224 at retainer groove 281, restricting axial movement of breakaway connector 224, as described further below.

Retainer fasteners 299 can be screws, bolts, pins, and the like, configured to be insertable into retainer bores 271 without extending substantially into central bore 225 and without contacting breakaway connector 224. Retainer fasteners therefore seal retainer bores 271 that are not used by retainer fastener 299.

Failsafe 210 can also differ in that failsafe 210 can include spring bores 273 configured to receive springs (discussed later). Spring bores 273 can include a counterbore at distal end 228 for receiving retainer plugs, as described further below.

Coupler 222 and transdermal implant 216 can be connected and operate consistently with coupler 22 and transdermal implant 16, respectively, as described in FIGS. 1-3B above. However, transdermal implant 216 can be sized larger than transdermal implant 16 to secure within proximal bore 244, where proximal bore 244 is larger than proximal bore 44. In some examples, proximal bore 244 can be of a diameter large enough to allow for breakaway connector 224 to be inserted into central bore 225 through second plate 218. Therefore, prosthetic 12 does not have to be removed from first plate 218 to replace breakaway connector 224. Instead, only transdermal implant 216 needs to be disconnected via coupler 222, which can save time and effort for a user after a breakaway incident.

Central bore 225 (FIG. 9) can bean annular bore through the center of bottom plate 218 coaxial with axis C, which can be a central axis of top plate 220 and bottom plate 218.

Proximal portion 227 can be a proximal side of bottom plate 218, where bottom plate 218 can engage top plate 220. Distal end 228 can be disposed at a distal end of bottom plate 218, opposite proximal portion 227.

Wings 230 (FIG. 8) can extend radially from the center of bottom plate 218, giving bottom plate 218 an X-like shape, in some examples, from a distal or proximal perspective. In some examples, there can be four of wings 230. In some other examples, wings 230 can have a quantity of 2, 3, 5, 6, and the like.

Proximal end 234 of top plate can be disposed opposite of distal portion 236. Distal portion 236 can be configured to engage proximal portion 227 of bottom plate 218. In some examples, distal portion 236 and proximal portion 227 can include flat surfaces substantially orthogonal to axis C, where the flat (or planar) surfaces can be configured to mate.

Distal portion 236 and proximal portion 227 can have other shapes in some other examples that are configured to engage or mate.

Wings 240 (FIG. 8) can extend radially from the center of top plate 220, giving top plate 220 an X-like shape from a distal or proximal perspective. In some examples, there can be four of wings 240. In some other examples, wings 240 can have a quantity of 2, 3, 5, 6, and the like. Each of wings 240 can include a bore or recess configured to receive detents, as discussed further below.

Central bore 242 (FIG. 9) of top plate 220 can be coaxial with central bore 225 of bottom plate 218 and central bores 242 and 225 can also be of the same diameter, such that when top plate 220 and bottom plate 218 engage, central bores 225 and 242 substantially align.

Counterbore 226 can also be an annular bore within top plate 220 that is coaxial with axis C and central bore 242. Counterbore 226 can have a diameter that is slightly larger than central bore 242, creating radial surface 280 that extends radially between central bore 242 and counterbore 226.

Proximal bore 244 (FIG. 9) can also be coaxial with central bores 225 and 242; however, proximal bore 244 can have a diameter that is of a different size, such as smaller or larger (as shown in the example of FIG. 9). Proximal bore 244 can extend substantially through a proximal portion of top plate 220 and can extend through proximal end 234, creating an annular opening at proximal end 234.

Breakaway connector 224 can have a generally cylindrical shape in some examples and can have other geometric shapes, such as a hexagonal prism, in other examples. Base 270 can be a cylindrical portion of breakaway connector 224 at the distal end of breakaway connector, where retainer groove 281 connects base 270 to arms 276a, 276b, 276c, 276d, 276e, and 276f (only arms 276a, 276b, and 276c are visible in FIG. 9). Retainer groove 281 can be a circumferential groove of a smaller diameter than base 270 and arms 276a-276f.

Arms 276a-276f can extend axially in a proximal direction from base 270. Proximate terminations of arms 276a-276f can include prongs 278a, 278b, 278c, 278d, 278e, and 278f (only prongs 278a, 278b, and 278c are visible in FIG. 9). Prongs 278a-278f can be radial extensions of arms 276a-276f, respectively, having a radial surface on a distal termination of each of prongs 278a-278f that can be configured to engage radial surface 280 of counterbore 226.

In assembly of one example, breakaway connector 224 can be inserted into proximal bore 244 with base 270 disposed near distal end 228 within central bore 225. In some examples, end bore 288 can be of a same diameter as central bore 225, so that breakaway retainer is also insertable through a distal end of central bore 225. As retainer groove 281 can be configured to receive breakaway retainer 297, breakaway retainer 297 can be threaded into one of retainer bores 271 to contact retainer groove 281 and can nest within retainer groove 281. In doing so, breakaway retainer 297 can apply a force on breakaway connector 224 forcing breakaway connector 224 distally. Forcing breakaway connector 224 distally forces prongs 278a-278f distally and causes prongs 278a-278f to contact radial surface 280 and/or central bore 242, securing breakaway connector 224 to bottom plate 218 and to top plate 220, which effectively can secure bottom plate 218 to top plate 220. This configuration of failsafe 210 can offer the benefit of assembly and reassembly of the components of failsafe 210 without tools, as breakaway retainer 271 can be operated by hand to secure breakaway connector 224 to top plate 220 and to bottom plate 218.

Following a breakaway event and separation of top plate 220 from bottom plate 218, transdermal implant 216 can be disengaged from top plate 220 using coupler 222. Breakaway connector 224 can then be inserted through proximal bore 244 and re-secured using breakaway retainer 297, as described above. Because lever 258 and breakaway retainer 297 can be operated using hands, tools are not required for disassembly and reassembly of failsafe 210. And, because breakaway connector 224 is insertable through proximal bore 244 of top plate 220, prosthetic 12 does not need to be disconnected from bottom plate 218 to reassemble failsafe 210.

Bottom plate 218 can be connected to a prosthetic appendage, such as prosthetic 12 of FIG. 8, using prosthetic bores 229. After assembly is complete, failsafe 210 can couple an appendage, such as appendage 14 of FIG. 8 to a prosthetic, such as prosthetic 12 of FIG. 8, while providing failsafe operation to protect transdermal implant 16, appendage 14, and other body parts of a patient from damage caused by forces transferred from prosthetic 12 to appendage 14 and from appendage 14 to prosthetic 12.

Failsafe 210 can be used consistently with failsafe 10 of FIGS. 1-3B above to secure prosthetic 12 to appendage 14 prevent damage to any one of prosthetic 12, appendage 14, implant 116, or any component or part within appendage 14 by limiting forces and moments transferred between prosthetic 12 and appendage 14.

Figure 10:
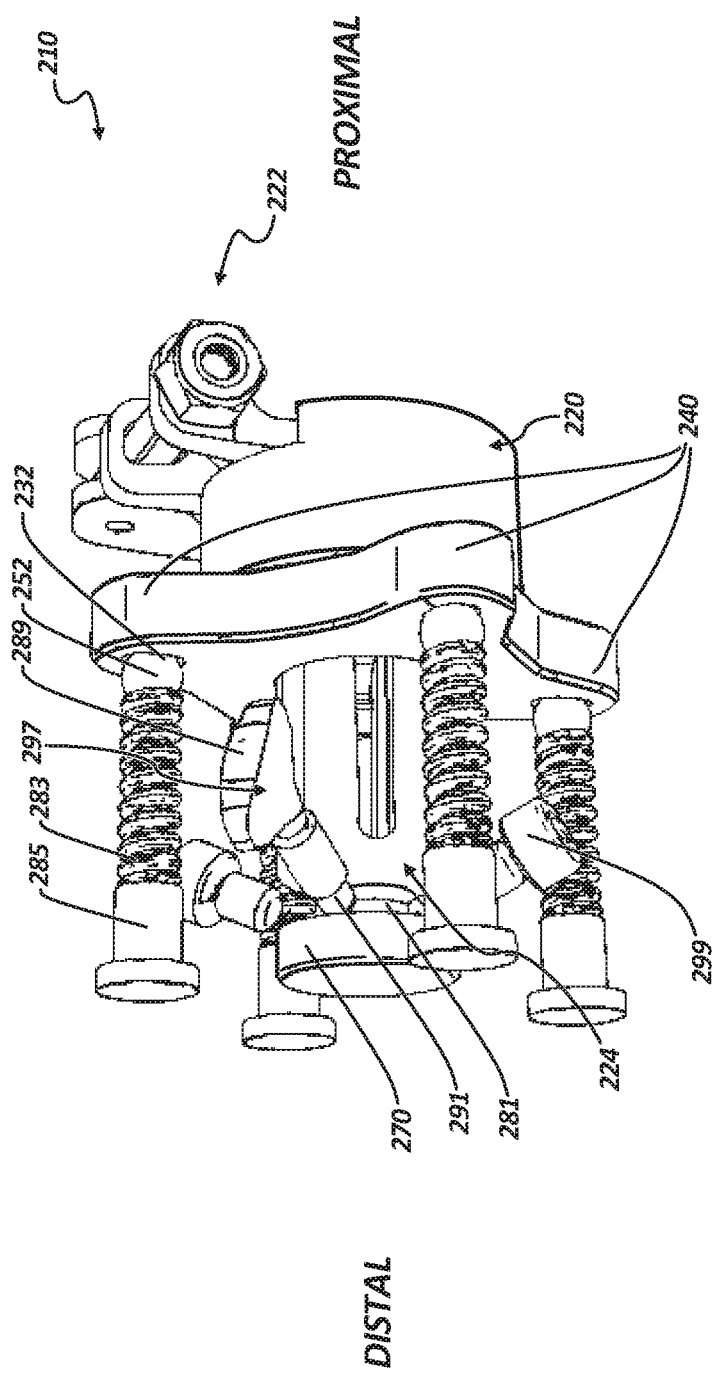
FIG. 10 shows an end view of a failsafe from a distal perspective, in accordance with at least one example of the present invention.
Figure 11:
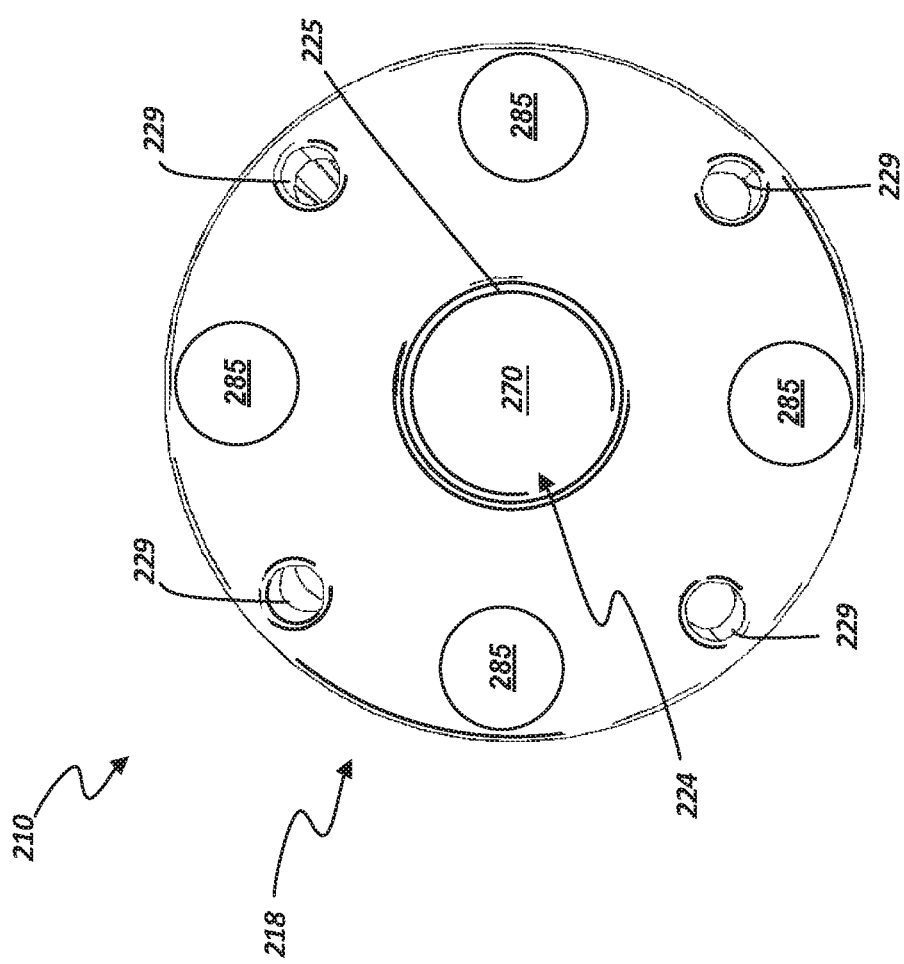
FIG. 11 shows an isometric view of a failsafe from a distal perspective, in accordance with at least one example of the present invention.

FIG. 10 shows an isometric view of failsafe 210 with transdermal implant 216 and bottom plate 218 removed for illustrative purposes. FIG. 11 shows an end view of failsafe 210 from a distal perspective. FIGS. 10 and 11 are discussed below concurrently.

Failsafe 210 can include bottom plate 218 (FIG. 11), top plate 220 (FIG. 10), coupler 222 (FIG. 10), breakaway connector 224, wings 240, detents 252 (FIG. 10), springs 283 (FIG. 10), spring retainers 285, retaining member 297 (FIG. 10), and retaining bolts 299 (FIG. 10). Bottom plate 218 (FIG. 11) can include central bore 225 and prosthetic bores 229 (FIG. 11). Breakaway connector 224 can include base 270 and retaining groove 281. Retaining member 297 can include thumb screw 289 and retaining portion 291.

Recesses 232 can be a negative geometry in the surface of each of wings 240 of top plate 220. Recesses 232 can be sized to receive detents 252, and can have a relatively sharp edge at a distal termination of recesses 232 for engaging detents 252. Detents 252 can be cylindrical ball bearings comprised of a rigid material, such as metal or polymer, in some examples, and can be of other shapes in some other examples. Springs 283 can be a biasing elements, such as a coil compression spring, in some examples, and can be other types of biasing elements, such as a compressible plastic or rubber, in other examples. Springs 283 can be configured to engage detents 252 to deliver a force to detents 252. Because springs 283 can be replaceable (or selectable), detents 252 can be customized to set a rotational force threshold or a desired torsional threshold. Spring retainers 285 can be press fit and/or welded into spring bores 273 to retain springs 283 and detents 252. Also, spring bores 273 may have a diametrically reduced bore proximate proximal portion 227 to retain detents 252 while allow a portion of detents 252 to extend beyond proximal portion 227 into recesses 232.

In operation of some examples, detents 252 can rest in recesses 232 to restrict relative rotation of top plate 220 to bottom plate 218 during normal operation. Then, when a threshold rotational force is applied to either of top plate 220 or bottom plate 218, recesses 232 can force detents 252 distally causing detents 252 to compress springs 283, allowing detents 252 to disengage recesses 232. When detents 252 disengage recesses 232, top plate 220 can rotate relative to bottom plate 218. In some examples, springs 283 can be selected to supply a desired threshold force. In some examples, springs 283 can be replaceable.

Retaining member 297 can include thumbscrew portion 289, which can be used to rotate retaining member 297 by hand in either rotational direction to threadably engage or disengage retaining bores 271. As retaining member 297 is threaded inward towards centerline C (of FIG. 9), retaining portion 291 of retaining member 297 will engage retaining groove 281. Retaining portion 291 can be sized to nest within retaining groove 281. As retaining portion 291 engages retaining groove 281, retaining member forces breakaway connector 224 distally, as discussed above, to securely couple bottom plate 218 to top plate 220.

Prosthetic bores 229 can be disposed on wings 240 of top plate 220. Prosthetic bores 229 can be sized to receive a fastener in some examples. For example, prosthetic bores 229 can be sized to receive a threaded fastener that is configured to engage a common size fastener for prosthetic limbs, such as prosthetic 12 of FIG. 8. Prosthetic bores 229 can be arranged in a pattern also common to prosthetic limbs.

Figure 12C:
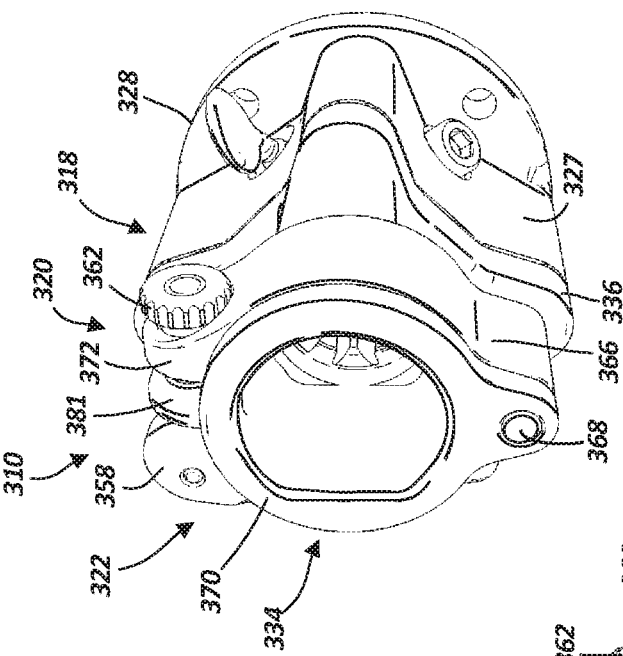
FIG. 12C shows an isometric view of a failsafe from a third distal perspective, in accordance with at least one example of the present invention.
Figure 12B:
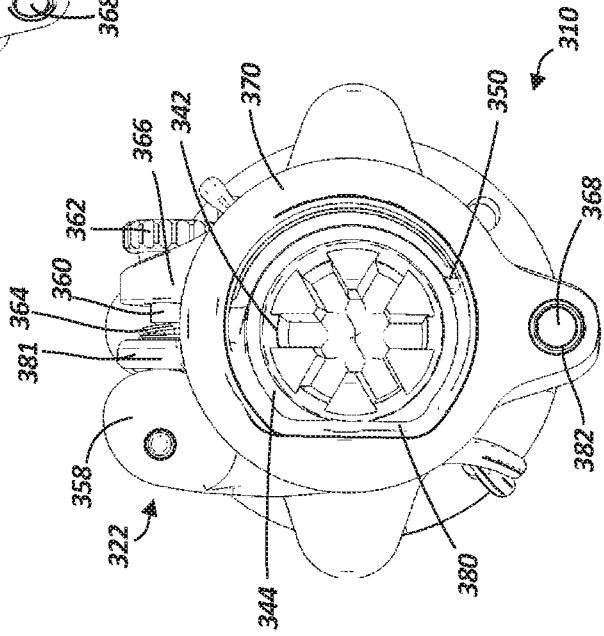
FIG. 12B shows an isometric view of a failsafe from a second distal perspective, in accordance with at least one example of the present invention.
Figure 12A:
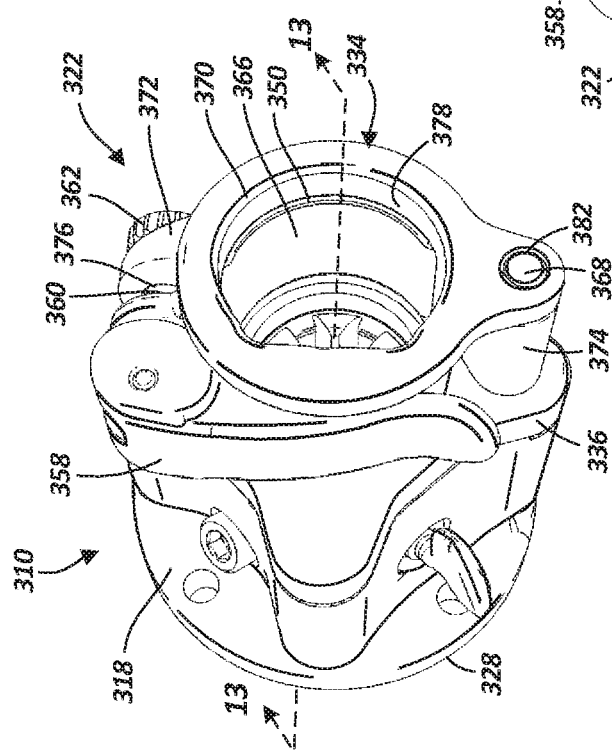
FIG. 12A shows an isometric view of a failsafe from a first distal perspective, in accordance with at least one example of the present invention.

FIG. 12A shows an isometric view of failsafe 310 from a first distal perspective, in accordance with at least one example of the present invention. FIG. 12B shows an isometric view of failsafe 310 from a second distal perspective, in accordance with at least one example of the present invention. FIG. 12C shows an isometric view of failsafe 310 from a third distal perspective, in accordance with at least one example of the present invention. FIGS. 12A-12C are discussed below concurrently. Failsafe 310 can be similar to failsafe 210 discussed above, except that coupler 322 can be different, as discussed in detail below.

Failsafe 310 can be connected to a prosthesis and an appendage (for example, prosthesis 12 and appendage 14 of FIG. 8). Failsafe 310 can include first plate (bottom plate) 318 (FIG. 12C), second plate (top plate) 320 (FIG. 12C), and coupler 322. Bottom plate 318 can include proximal portion 327, and distal end 328. Top plate 320 can include proximal end 334, distal portion 336, central bore 342 (FIG. 12B), proximal bore 344 (FIG. 12B), and arm slot 350. Coupler 322 can include lever 358, cam 360, nut 362, spring 364, arm 366, pin 368, and collar 370. Arm 366 can include flange 372 and coupling portion 374. Flange 372 can include eye 376. Collar 370 can include bore 378, flat portion 380, collar flange 381, and pin bore 382.

Top plate 320 can be consistent with top plate 220, discussed above, except top plate 320 can differ in that it can include collar 370 (discussed below) and central bore 342. Central bore 342 can include arm slot 350. Arm slot 350 can be an axially extending and partial-circumferential slot, or portion of top plate 320 that is removed or missing, and can be shaped to receive arm 366 therein. Arm slot 350 can be sized to limit the extension of arm 366 into central 342.

Lever 358 can be an arm or handle pivotably coupled to cam 360. In some examples, lever 358 can be pinned to cam 360 and in other examples, lever 358 can be releasably secured to cam 360 using, for example, a fastener such as a screw or bolt. In yet other examples, lever 358 and cam 360 can be formed of a single piece.

Lever 358 and cam 360 can be comprised of rigid or semi-rigid materials such as metals, plastics, composites, combinations thereof, and the like. Cam 360 can be a rod or other elongate body and can include a threaded portion at an end opposite lever 358. The threaded portion can be configured to releasably engage nut 362. In other examples, nut 362 can be a bolt that threadably engages a female threaded portion of cam 360.

In some examples, nut 362 can be knurled to improve friction for tool-less operation (finger tightening and loosening). However, nut 362 can have other shapes and profiles in other examples to allow tool-less operation (e.g., wing nut). Spring 364 (biasing element) can be a spring or other elastic member configured to store and release mechanical energy. In some examples, spring 364 can be a compression coil spring disposed around cam 360 between lever 358 and nut 362.

Arm 366 can be a rotating arm coupleable to collar 370 using pin 368 at coupling portion 374 of arm 366, which can receive pin 368 therein. In some examples, pin 368 can be other types of fasteners configured to enable hinging or rotation of arm 366, such as a screw, bolt, rivet, hinge, and the like. Arm 366 can include flange 372 on an end opposite of coupling portion 374. Flange 372 can include eye 376 sized and configured to receive cam 360 therethrough.

Collar 370 can include bore 378 sized and configured to receive a transdermal implant (as shown below). Bore 378 can include flat portion 380 to interface with a flat portion or side of the transdermal implant to ensure that the transdermal implant is inserted into bore 378 at a preferred orientation. Collar flange 381 can be positioned opposite of pin bore 382 and can include an eye or aperture sized to receive cam 360 therethrough. Collar flange 381 can also include a face contoured and configured to engage lever 358 such that lever 358 can actuate against the face of collar flange 381 to lock arm 366 in a desired position, as discussed further below.

Spring 364 can be disposed between collar flange 381 and nut 360 in some examples. In these examples, nut 362 can have a tapered surface configured to engage the spring and eye 376. In this example, eye 376 can have a tapered surface complementary to nut 362, which can help to prevent back-out of nut 362 by increasing contact surface area between the complementary tapered surfaces of nut 362 and eye 376. In other examples, spring 364 can be configured to engage collar flange 381 and flange 372.

In operation of some examples, cam 360 (which can be previously coupled to lever 358) can be inserted through collar flange 381 and spring 364 can be placed over cam 360. Then, arm 366 can be pivoted to a closed position about pin 368, as shown in FIGS. 12A-12C, and cam 360 can be passed through or into flange 372. Nut 362 can then be threaded onto cam 360 to a desired torque to engage spring 364 and eye 376. Once nut 362 is secured to cam 360, lever 358 can be actuated from an open position to a closed position (as shown in FIGS. 12A-12C), drawing arm 366 into arm slot 350 of top plate 320 to apply a force on the transdermal implant, which is restrained from rotation by flat face 380.

An amount that arm 366 extends into central bore 342 of through arm slot 350 can be adjusted by tightening nut 362 while lever 358 is in the closed position. In other examples, the amount arm 366 extends into central bore 342 through arm slot 350 can be adjusted by opening lever 358, tightening nut 362, and reclosing lever 358. In both examples, the amount arm 366 extends into central bore 342 of through arm slot 350 can adjustable to alter a clamping force applied to the transdermal implant by arm 366. This adjustability can help compensate for variance in the size and shape of transdermal implants that can occur due to tolerance, variance between manufacturers, and/or changes in shape and size due to wear.

In an operation of opening lever 358, spring 364 will force nut 362 and therefore cam 360 and lever 358 and arm 366 to an open position, forcing arm 366 out of (or partially out of) arm slot 350, and removing (or reducing) the force applied by arm 366 on the transdermal implant and allowing the transdermal implant to be quickly removed from central bore 342.

By providing arm 366 that has a relatively long axial length relative to a length of top plate 320, arm 366 can apply a clamping force over a relatively large surface area to help reduce wear on the transdermal implant. Because the area of arm 366 contacting the transdermal implant is relatively large, the pressure applied to the transdermal implant for a given force can be reduced, allowing a larger force to be applied while avoiding damage to the transdermal implant. Further, because arm 366 provides a large contact surface with the transdermal implant, arm 366 can be used to engage transdermal implants varying in geometry and wear. Also, because lever 358 and nut 362 can be operated using a hand, breakaway connector 310 can be secured to a transdermal implant without the use of tools.

Figure 13B:
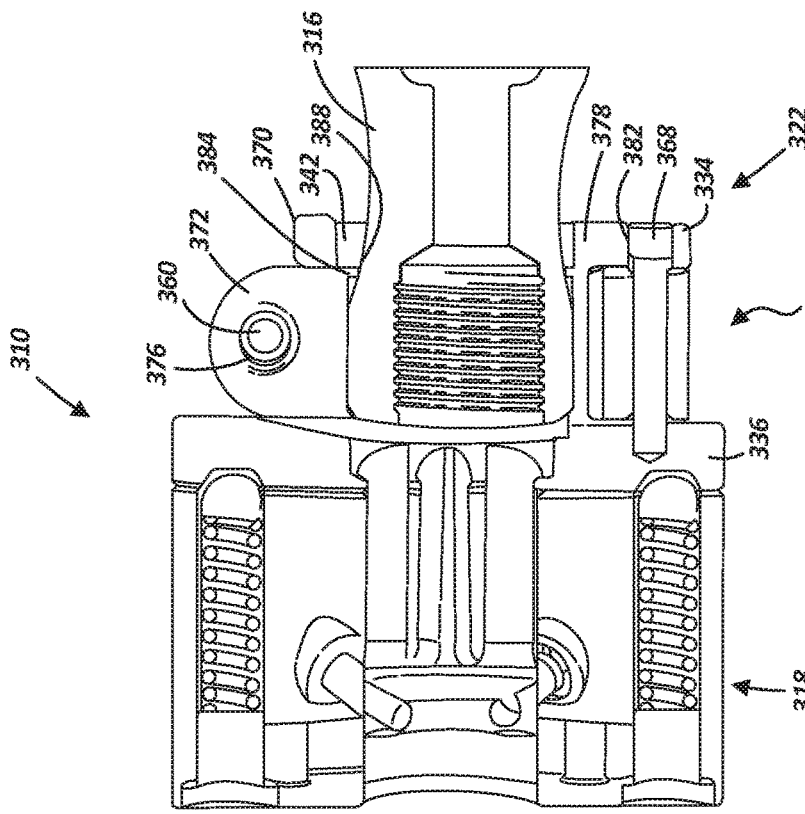
FIG. 13B shows a cross-sectional view of a failsafe for a prosthetic limb across section 13 of FIG. 12A with a transdermal implant, in accordance with at least one example of the present invention.
Figure 13A:
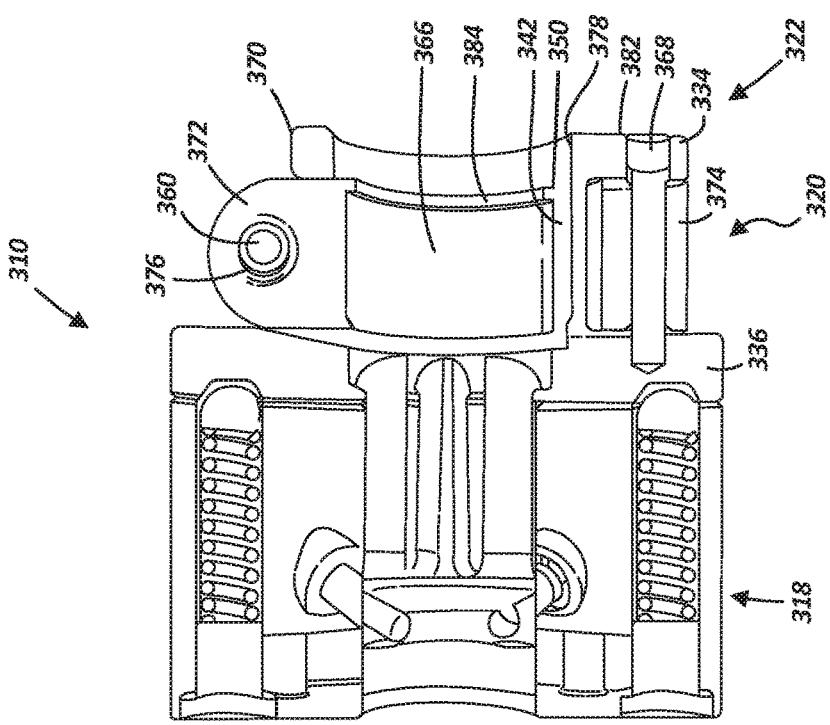
FIG. 13A shows a cross-sectional view of a failsafe for a prosthetic limb across section 13 of FIG. 12A, in accordance with at least one example of the present invention.

FIG. 13A shows a cross-sectional view of failsafe 310 for a prosthetic limb across section 13 of FIG. 12A, in accordance with at least one example of the present invention. FIG. 13B shows a cross-sectional view of failsafe 310 for a prosthetic limb across section 13 of FIG. 12A with transdermal implant 316, in accordance with at least one example of the present invention. FIGS. 13A and 13B are discussed concurrently below.

Failsafe 310 can be connected to a prosthesis and transdermal implant 316 (for example, prosthesis 12 of FIG. 8). Failsafe 310 can include first plate (bottom plate) 318 (FIG. 12C), second plate (top plate) 320 (FIG. 12C), and coupler 322. Top plate 320 can include proximal end 334, distal portion 336, bore 342 (FIG. 12B), and arm slot 350. Coupler 322 can include cam 360, arm 366, pin 368, and collar 370. Arm 366 can include flange 372, coupling portion 374, and lip 384. Flange 372 can include eye 376. Collar 370 can include bore 378 and pin bore 382. Transdermal implant 316 can include necked portion 388.

Failsafe 310 as shown in FIGS. 13A and 13B can be similar to failsafe 310 of FIGS. 12A-12C. However, FIGS. 13A-13B show additional details of failsafe 310. For example, FIGS. 13A and 13B show how pin 368 extends into pin bore 382, which can extend from collar 370, into coupling portion 374 of arm 366, and into distal portion 336 of top plate 320. Pin 368 can thereby pivotably couple arm 366 to color 370 and distal portion 336 of top plate 320.

FIGS. 13A and 13B also show how arm 366 engages transdermal implant 316. Lip 384 can be a protrusion extending from arm 366 radially inward and for a relatively short axial length of arm 366, in some examples. When transdermal implant 316 is inserted into central bore 342 and arm 366 is closed (as shown in FIG. 13B), lip 384 can engage necked portion 388 of transdermal implant 316, which can limit axial movement of transdermal implant 316 relative to top plate 320. In this way, friction applied by arm 366 can reduce axial movement and rotation of transdermal implant 316 relative to top plate 320, while flat portion 380 prevents rotation of transdermal implant 316 relative to top plate 320 and lip 384 prevents axial movement of implant 316 relative to top plate 320, in total providing redundant protection from relative rotation and axial movement of implant 316 relative to top plate 320.

Figure 14:
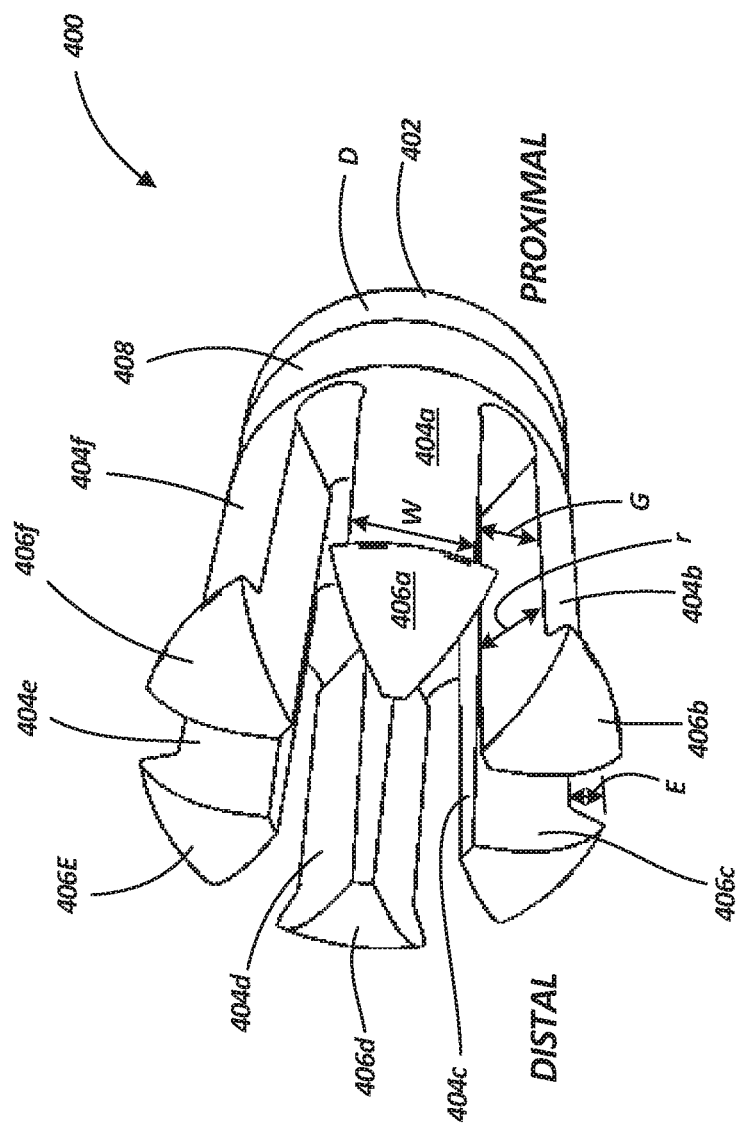
FIG. 14 shows an isometric view of a breakaway connector, in accordance with at least one example of the present invention.

FIG. 14 shows an isometric view of breakaway connector 400, in accordance with at least one example of the present invention.

Breakaway connector 400 can include base 402, arms 404a, 404b, 404c, 404d, 404e, and 404f, prongs 406a, 406b, 406c, 406d, 406e, and 406f, and recessed portion (or circumferential groove or retainer groove) 408. Also shown in FIG. 14 is diameter D, circumferential width w, gap G, radial thickness r, prong extension E, and orientation indicators Proximal and Distal.

As discussed above, breakaway connector 400 can be a central cantilevered spring, in some examples, comprised of a material having an elastic deformation range suitable to deflect as described herein without deforming. In some examples, breakaway connector can be comprised of steel alloys, titanium alloys, and cobalt alloys. In some examples, breakaway connector can be comprised of a titanium alloy such as Ti-6Al-4V.

Breakaway connector 400 can include base 400 which can be connected to arms 404a-404e. Arms 404a-404e can each extend distally from base 402 and can be connected to base 402 at circumferential groove 408. Base 402 can have a diameter D, which can be the same as the diameter of arms 404a-404f, in some examples. Each of arms 404a-404f can have a circumferential width w and a radial thickness r and can each be spaced apart by gap G. For example, arms 404a and 404b are separated by gap G.

Each of prongs 406a-406f can extend radially outward from arms 404a-404f, respectively, by prong extension E. In some examples, the prong extension E of each of prongs 406a-406f can determine the moment required for breakaway connector 400 to allow separation of a top and bottom plate. Because, as E increases, larger deflection, and therefore a larger moment, is required for prongs 406a-406f to disengage the radial surface of the counterbore they engage, as discussed above. Therefore, when extension E is larger, a larger moment can be required to cause a larger deflection of an arms before breakaway; and, when extension E is smaller, a smaller moment can be required to cause a smaller deflection of the arms before breakaway. In this way, the moment required to cause breakaway can be selected based on the extension E of each of prongs 406a-406f. In some examples, a kit can include more than one breakaway connector, where each has a different extension E to provide a physician selectable breakaway moment. In other examples, a kit including multiple breakaway connectors can be provided to a user to be paired with different prostheses or to be changed out for different activities (e.g., walking versus running).

In other examples, the required moment to cause breakaway can be varied by adjusting other aspects of breakaway connector 400. For example, diameter D of the arms can be adjusted to be larger or smaller. Also, the circumferential width w of each arm can be adjusted along with the gap G between each of arms 404a-404f. In other examples, when the circumferential width w is adjusted, the number of arms can also be adjusted between 2, 3, 4, 5, 6, 7, 8, 9, 10, and the like. In other examples, radial thickness r of each of arms 404a-404f can be adjusted to adjust the moment required to cause breakaway of the top plate from the bottom plate.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A failsafe for a transdermal implant for a prosthesis, the failsafe comprising:
   a first plate defining a central axis, the first plate comprising:
   a proximal portion;
   and a distal portion securable with the prosthesis configured to be disposed external to skin, the prosthesis configured to simulate an appendage of a patient;
   a second plate alignable with the central axis, the second plate comprising:
   a distal portion configured to interface with the proximal portion of the first plate;
   and a proximal portion securable to the transdermal implant;
   a breakaway connector positionable at least partially within the second plate and the first plate, the breakaway connector configured to engage the second plate to secure the first plate to the second plate, and at least a portion of the breakaway connector configured to break away from the first plate when a moment applied to the second plate is larger than a threshold moment;
   and a knob securable to the breakaway connector and the knob operable to secure the first plate to the second plate via the breakaway connector.

2. The failsafe of claim 1, wherein the knob is operable without the use of a tool to secure the knob to the breakaway connector.

3. The failsafe of claim 2, wherein the knob is threadably securable to the breakaway connector.

4. The failsafe of claim 2, wherein the knob includes an extension extending from a proximal portion of the knob, the extension engageable with the breakaway connector to secure the knob to the breakaway connector.

5. The failsafe of claim 4, wherein the extension of the knob is threaded and is threadably securable to a threaded portion of the breakaway connector.

6. The failsafe of claim 5, wherein the extension of the knob is insertable through a bore in the distal portion of the first plate to engage the breakaway connector.

7. The failsafe of claim 6, wherein the breakaway connector further comprises:
   a base and
   a plurality of arms projecting axially from the base and extending between the second plate and the first plate.

8. The failsafe of claim 7, wherein the base of the breakaway connector includes the threaded portion of the breakaway connector.

9. The failsafe of claim 8, wherein the plurality of arms each comprise a prong located at a termination of each arm, each of the prongs extending radially outward from each of the arms to create a radial extension.

10. The failsafe of claim 9, wherein each radial extension of each of the prong is configured to engage a radial surface of a counterbore of one of the first plate and the second plate to engage the first plate and the second plate.

11. The failsafe of claim 1, wherein the knob is securable to the prosthetic appendage.

12. The failsafe of claim 1, further comprising:
   a plurality of recesses in the proximal portion of the first plate; and
   a plurality of retaining members extending from the second plate and configured to engage the recesses to transfer torque between the first plate and second plate when a torque is below a threshold torque and configured to disengage from the recesses and allow rotation of the first plate relative to the second plate when an applied torque is above the threshold torque.

13. A failsafe for a transdermal implant for a prosthesis that is configured to be disposed external to skin, the failsafe comprising:
   a first plate defining a central axis, the first plate comprising:
   a proximal portion and a distal portion securable with the prosthesis; and
   a second plate alignable with the central axis, the second plate comprising:
   a distal portion configured to interface with the proximal portion of the first plate; and
   a proximal portion securable to the transdermal implant;
   a breakaway connector located at least partially within the second plate and the first plate, the breakaway connector configured to engage the second plate to secure the first plate to the second plate, and at least a portion of the breakaway connector configured to break away from the first plate when a moment applied to the second plate is larger than a threshold moment; and a knob secured to the breakaway connector to secure the first plate to the second plate.

14. The failsafe of claim 13, wherein the knob is operable by hand to secure the knob to the breakaway connector.

15. The failsafe of claim 14, wherein the knob includes an extension extending from a proximal portion of the knob, the extension engaged with the breakaway connector to secure the knob to the breakaway connector.

16. The failsafe of claim 15, wherein the extension of the knob is threaded and is threadably engaged with a threaded portion of the breakaway connector.

17. The failsafe of claim 16, wherein an outer surface of the knob is crenulated.

18. The failsafe of claim 13, wherein the knob is secured to the prosthetic appendage.

19. A failsafe for a transdermal implant for a prosthesis that is configured to be disposed external to skin, the failsafe comprising:

a first plate comprising a proximal portion and a distal portion securable with the prosthesis;

a second plate comprising:

a distal portion configured to interface with the proximal portion of the first plate;

and a proximal portion securable to the transdermal implant;

a breakaway connector positionable at least partially within the second plate and the first plate, the breakaway connector configured to engage the second plate to secure the first plate to the second plate, and at least a portion of the breakaway connector configured to break away from the first plate when a moment applied to the second plate is larger than a threshold moment;

and a knob securable to the breakaway connector and the knob operable to secure the first plate to the second plate.

20. The failsafe of claim 19, wherein the knob includes a threaded extension extending from a proximal portion of the knob, the knob insertable through a bore in the distal portion of the first plate to threadably secure the threaded extension to a threaded portion of the breakaway connector.

* * * * *